(12) United States Patent
Wright et al.

(10) Patent No.: US 9,861,933 B2
(45) Date of Patent: *Jan. 9, 2018

(54) METHOD AND APPARATUS FOR EXTRACTING CARBON DIOXIDE FROM AIR

(71) Applicant: Carbon Sink, Inc., Huntington, NY (US)

(72) Inventors: Allen B. Wright, Tucson, AZ (US); Klaus S. Lackner, Dobbs Ferry, NY (US); Ursula Ginster, Tucson, AZ (US)

(73) Assignee: CARBON SINK, INC., Huntington, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/243,806

(22) Filed: Aug. 22, 2016

(65) Prior Publication Data

US 2017/0028347 A1 Feb. 2, 2017

Related U.S. Application Data

(60) Continuation of application No. 14/986,830, filed on Jan. 4, 2016, now abandoned, which is a continuation
(Continued)

(51) Int. Cl.
*B01D 53/02* (2006.01)
*B01D 53/62* (2006.01)
(Continued)

(52) U.S. Cl.
CPC .............. *B01D 53/62* (2013.01); *A01G 7/02* (2013.01); *A01G 9/18* (2013.01); *A01G 9/246* (2013.01);
(Continued)

(58) Field of Classification Search
CPC ................ A01G 9/18; B01D 2253/206; B01D 2257/504; B01D 53/047; B01D 53/22;
(Continued)

(56) References Cited

U.S. PATENT DOCUMENTS 1,031,799 A 7/1912 Mackay
1,296,889 A 3/1919 White
(Continued)

FOREIGN PATENT DOCUMENTS

CA 1212522 A1 10/1986
CA 1236877 A1 5/1988
(Continued)

OTHER PUBLICATIONS

Dubey, Science for sustainability: From capturing carbon dioxide from air to environmental impact of a hydrogen economy, Apr. 2003.*
(Continued)

*Primary Examiner* — Christopher P Jones
(74) *Attorney, Agent, or Firm* — Wilson Sonsini Goodrich & Rosati

(57) ABSTRACT

A method and apparatus for extracting $CO_2$ from air comprising an anion exchange material formed in a matrix exposed to a flow of the air, and for delivering that extracted $CO_2$ to controlled environments. The present invention contemplates the extraction of CO2 from air using conventional extraction methods or by using one of the extraction methods disclosed; e.g., humidity swing or electro dialysis. The present invention also provides delivery of the $CO_2$ to greenhouses where increased levels of $CO_2$ will improve conditions for growth. Alternatively, the $CO_2$ is fed to an algae culture.

20 Claims, 15 Drawing Sheets

Related U.S. Application Data of application No. 14/183,751, filed on Feb. 19, 2014, now Pat. No. 9,266,052, which is a continuation of application No. 13/796,855, filed on Mar. 12, 2013, now abandoned, which is a continuation of application No. 12/903,958, filed on Oct. 13, 2010, now abandoned, which is a continuation of application No. 12/638,717, filed on Dec. 15, 2009, now abandoned, which is a division of application No. 11/866,326, filed on Oct. 2, 2007, now Pat. No. 7,708,806.

(60) Provisional application No. 60/829,376, filed on Oct. 13, 2006, provisional application No. 60/827,849, filed on Oct. 2, 2006.

(51) Int. Cl.

| | | |
|---|---|---|
| *B01D 53/04* | (2006.01) | |
| *C12M 1/00* | (2006.01) | |
| *A01G 9/18* | (2006.01) | |
| *B01D 53/047* | (2006.01) | |
| *B01D 53/22* | (2006.01) | |
| *A01G 7/02* | (2006.01) | |
| *A01G 9/24* | (2006.01) | |
| *A01G 33/00* | (2006.01) | |
| *B01D 53/14* | (2006.01) | |
| *B01D 61/42* | (2006.01) | |
| *B01J 47/14* | (2017.01) | |
| *C12M 1/107* | (2006.01) | |
| *B01J 41/05* | (2017.01) | |
| *C01B 32/50* | (2017.01) | |

(52) U.S. Cl.
CPC .............. *A01G 33/00* (2013.01); *B01D 53/04* (2013.01); *B01D 53/047* (2013.01); *B01D 53/1425* (2013.01); *B01D 53/1493* (2013.01); *B01D 53/22* (2013.01); *B01D 61/422* (2013.01); *B01J 41/05* (2017.01); *B01J 47/14* (2013.01); *C01B 32/50* (2017.08); *C12M 21/02* (2013.01); *C12M 23/18* (2013.01); *C12M 23/36* (2013.01); *C12M 29/00* (2013.01); *B01D 2252/10* (2013.01); *B01D 2252/204* (2013.01); *B01D 2252/30* (2013.01); *B01D 2253/206* (2013.01); *B01D 2257/504* (2013.01); *B01D 2258/06* (2013.01); *B01D 2325/38* (2013.01); *Y02C 10/04* (2013.01); *Y02C 10/06* (2013.01); *Y02C 10/08* (2013.01); *Y02C 10/10* (2013.01); *Y02E 50/343* (2013.01); *Y02P 20/152* (2015.11); *Y02P 60/247* (2015.11)

(58) Field of Classification Search
CPC ........ B01D 53/62; C01B 31/20; C12M 21/02; Y02C 10/04; Y02C 10/06; Y02C 10/08; Y02C 10/10
See application file for complete search history.

(56) References Cited

U.S. PATENT DOCUMENTS

| | | | |
|---|---|---|---|
| 1,482,367 A | 1/1924 | Elledge | |
| 2,718,454 A | 9/1955 | Wylie | |
| 2,796,145 A | 6/1957 | King | |
| 2,922,489 A | 1/1960 | Hollingsworth | |
| 3,024,207 A * | 3/1962 | Shaw | B01J 47/007 |
| | | | 521/134 |
| 3,063,195 A | 11/1962 | Ravich | |
| 3,111,485 A | 11/1963 | Kunin | |
| 3,282,831 A | 11/1966 | Hamm | |
| 3,294,488 A | 12/1966 | Dunlop | |
| 3,318,588 A | 5/1967 | Russell | |
| 3,330,750 A * | 7/1967 | McRae | B01D 61/48 |
| | | | 204/524 |
| 3,344,050 A | 9/1967 | Mayland | |
| 3,466,019 A | 9/1969 | Priestley | |
| 3,466,138 A * | 9/1969 | Routsis | H01M 8/0662 |
| | | | 423/230 |
| 3,470,708 A | 10/1969 | Weil et al. | |
| 3,489,506 A | 1/1970 | Galstaun et al. | |
| 3,498,026 A | 3/1970 | Messinger et al. | |
| 3,554,691 A | 1/1971 | Kuo et al. | |
| 3,556,716 A | 1/1971 | Pollio et al. | |
| 3,561,926 A | 2/1971 | Mcelroy | |
| 3,594,989 A | 7/1971 | Bastiaans | |
| 3,627,478 A * | 12/1971 | Tepper | B01D 53/02 |
| | | | 423/228 |
| 3,627,703 A | 12/1971 | Kojima et al. | |
| 3,632,519 A * | 1/1972 | Gustafson | A62B 21/00 |
| | | | 252/189 |
| 3,645,072 A | 2/1972 | Clapham | |
| 3,691,109 A | 9/1972 | Larsen | |
| 3,710,778 A | 1/1973 | Cornelius | |
| 3,712,025 A | 1/1973 | Wallace | |
| 3,727,375 A * | 4/1973 | Wallace | B01D 53/62 |
| | | | 95/139 |
| 3,833,710 A | 9/1974 | Deschamps et al. | |
| 3,841,558 A | 10/1974 | Fowler et al. | |
| 3,848,577 A | 11/1974 | Storandt | |
| 3,855,001 A * | 12/1974 | Cheron | B01D 53/14 |
| | | | 429/410 |
| 3,865,924 A | 2/1975 | Gidaspow et al. | |
| 3,876,565 A | 4/1975 | Takashima et al. | |
| 3,876,738 A | 4/1975 | Marinaccio et al. | |
| 3,880,981 A | 4/1975 | Garingarao et al. | |
| 3,891,411 A | 6/1975 | Meyer | |
| 3,907,967 A | 9/1975 | Filss | |
| 3,915,822 A | 10/1975 | Veltman | |
| 3,948,627 A | 4/1976 | Schwarz et al. | |
| 3,981,698 A | 9/1976 | Leppard | |
| 4,012,206 A * | 3/1977 | Macriss | B01D 53/06 |
| | | | 95/113 |
| 4,047,894 A | 9/1977 | Kuhl | |
| 4,138,850 A * | 2/1979 | Tchernev | F24J 2/04 |
| | | | 417/53 |
| 4,140,602 A | 2/1979 | Lewis et al. | |
| 4,167,551 A | 9/1979 | Tamura et al. | |
| 4,197,421 A | 4/1980 | Steinberg | |
| 4,238,305 A | 12/1980 | Gancy et al. | |
| 4,239,515 A | 12/1980 | Futami et al. | |
| 4,246,241 A | 1/1981 | Mathur et al. | |
| 4,249,317 A | 2/1981 | Murdock | |
| 4,264,340 A * | 4/1981 | Sircar | B01D 53/0476 |
| | | | 95/122 |
| 4,296,050 A | 10/1981 | Meier | |
| 4,321,410 A | 3/1982 | Ono et al. | |
| 4,336,227 A | 6/1982 | Koyama et al. | |
| 4,340,480 A | 7/1982 | Pall et al. | |
| 4,398,927 A | 8/1983 | Asher et al. | |
| 4,409,006 A | 10/1983 | Mattia | |
| 4,425,142 A | 1/1984 | Mann | |
| 4,436,707 A | 3/1984 | Karwat | |
| 4,475,448 A | 10/1984 | Shoaf et al. | |
| 4,497,641 A | 2/1985 | Brown, Jr. et al. | |
| 4,511,375 A | 4/1985 | BeVier | |
| 4,528,248 A | 7/1985 | Galbraith | |
| 4,543,112 A | 9/1985 | Ackley et al. | |
| 4,566,221 A | 1/1986 | Kossin | |
| 4,569,150 A | 2/1986 | Carlson et al. | |
| 4,592,817 A | 6/1986 | Chlanda et al. | |
| 4,594,081 A | 6/1986 | Kroll et al. | |
| 4,608,140 A | 8/1986 | Goldstein | |
| 4,678,648 A | 7/1987 | Wynn | |
| 4,711,097 A | 12/1987 | Besik | |
| 4,711,645 A | 12/1987 | Kumar | |
| 4,729,883 A | 3/1988 | Lam et al. | |
| 4,735,603 A | 4/1988 | Goodson et al. | |
| 4,770,777 A | 9/1988 | Steadly et al. | |

(56) References Cited

U.S. PATENT DOCUMENTS

| | | | |
|---|---|---|---|
| 4,804,522 A | 2/1989 | Hass | |
| 4,810,266 A | 3/1989 | Zinnen et al. | |
| 4,861,360 A | 8/1989 | Apffel | |
| 4,869,894 A | 9/1989 | Wang et al. | |
| 4,899,544 A | 2/1990 | Boyd | |
| 4,906,263 A | 3/1990 | Von Blucher et al. | |
| 4,941,898 A | 7/1990 | Kimura | |
| 4,946,620 A | 8/1990 | Kadono et al. | |
| 4,953,544 A | 9/1990 | Hansen et al. | |
| 4,957,519 A | 9/1990 | Chen | |
| 4,980,098 A | 12/1990 | Connery | |
| 5,069,688 A * | 12/1991 | Wells | B01D 53/0473 95/130 |
| 5,070,664 A | 12/1991 | Groh et al. | |
| 5,170,633 A | 12/1992 | Kaplan | |
| 5,180,750 A | 1/1993 | Sugaya et al. | |
| 5,203,411 A | 4/1993 | Dawe et al. | |
| 5,215,662 A | 6/1993 | Johnson et al. | |
| 5,232,474 A * | 8/1993 | Jain | B01D 53/047 95/122 |
| 5,253,682 A | 10/1993 | Haskett et al. | |
| 5,277,915 A | 1/1994 | Provonchee et al. | |
| 5,281,254 A | 1/1994 | Birbara et al. | |
| 5,304,234 A | 4/1994 | Takatsuka et al. | |
| 5,308,466 A * | 5/1994 | Ganzi | B01D 61/48 204/524 |
| 5,316,637 A * | 5/1994 | Ganzi | B01D 61/48 204/533 |
| 5,318,758 A | 6/1994 | Fujii et al. | |
| 5,328,851 A | 7/1994 | Zaromb | |
| 5,344,627 A | 9/1994 | Fujii et al. | |
| 5,385,610 A | 1/1995 | Deerer et al. | |
| 5,389,257 A | 2/1995 | Todd et al. | |
| 5,401,475 A | 3/1995 | Ayala et al. | |
| 5,409,508 A | 4/1995 | Erickson | |
| 5,414,957 A | 5/1995 | Kenney | |
| 5,443,740 A | 8/1995 | Schmitt | |
| 5,454,189 A | 10/1995 | Graham et al. | |
| 5,520,894 A | 5/1996 | Heesink et al. | |
| 5,525,237 A | 6/1996 | Birbara et al. | |
| 5,535,989 A | 7/1996 | Sen | |
| 5,658,372 A | 8/1997 | Gadkaree | |
| 5,659,974 A | 8/1997 | Graeff | |
| 5,682,709 A * | 11/1997 | Erickson | A01G 7/02 47/1.4 |
| 5,711,770 A | 1/1998 | Malina | |
| 5,747,042 A | 5/1998 | Choquet | |
| 5,756,207 A | 5/1998 | Clough et al. | |
| 5,779,767 A | 7/1998 | Golden et al. | |
| 5,788,826 A * | 8/1998 | Nyberg | B01J 47/08 204/536 |
| 5,792,440 A | 8/1998 | Huege | |
| 5,797,979 A * | 8/1998 | Quinn | B01D 53/02 95/102 |
| 5,833,747 A | 11/1998 | Bleakley et al. | |
| 5,876,488 A | 3/1999 | Birbara et al. | |
| 5,887,547 A | 3/1999 | Caveny et al. | |
| 5,914,455 A | 6/1999 | Jain et al. | |
| 5,917,136 A | 6/1999 | Gaffney et al. | |
| 5,934,379 A | 8/1999 | Oestlyngen et al. | |
| 5,955,043 A | 9/1999 | Neuman et al. | |
| 5,962,545 A | 10/1999 | Chaudhary et al. | |
| 5,972,080 A | 10/1999 | Nagata | |
| 5,980,611 A | 11/1999 | Kumar et al. | |
| 6,004,381 A | 12/1999 | Rohrbach et al. | |
| 6,027,552 A | 2/2000 | Ruck et al. | |
| 6,048,509 A | 4/2000 | Kawai et al. | |
| 6,083,740 A | 7/2000 | Kodo et al. | |
| 6,117,404 A | 9/2000 | Mimura et al. | |
| 6,136,075 A | 10/2000 | Bragg et al. | |
| 6,143,057 A * | 11/2000 | Bulow | B01D 53/02 502/79 |
| 6,158,623 A | 12/2000 | Benavides et al. | |
| 6,180,012 B1 | 1/2001 | Rongved | |
| 6,200,543 B1 | 3/2001 | Allebach et al. | |
| 6,209,256 B1 | 4/2001 | Brittin et al. | |
| 6,214,303 B1 | 4/2001 | Hoke et al. | |
| 6,221,225 B1 | 4/2001 | Mani | |
| 6,228,145 B1 | 5/2001 | Falk-Pedersen et al. | |
| 6,237,284 B1 * | 5/2001 | Erickson | A01G 7/02 47/1.5 |
| 6,279,576 B1 | 8/2001 | Lambert | |
| 6,284,021 B1 | 9/2001 | Lu et al. | |
| 6,306,803 B1 | 10/2001 | Tazaki | |
| 6,316,668 B1 | 11/2001 | King et al. | |
| 6,322,612 B1 | 11/2001 | Sircar et al. | |
| 6,334,886 B1 | 1/2002 | Barnes, Jr. et al. | |
| 6,346,938 B1 | 2/2002 | Chan et al. | |
| 6,364,938 B1 | 4/2002 | Birbara et al. | |
| 6,402,819 B1 | 6/2002 | De Ruiter et al. | |
| 6,500,236 B2 | 12/2002 | Suzuki et al. | |
| 6,503,957 B1 * | 1/2003 | Bernatowicz | C08J 5/2275 521/25 |
| 6,526,699 B1 | 3/2003 | Foglio, Sr. | |
| 6,547,854 B1 | 4/2003 | Gray et al. | |
| 6,565,627 B1 | 5/2003 | Golden et al. | |
| 6,582,498 B1 | 6/2003 | Sass et al. | |
| 6,617,014 B1 | 9/2003 | Thomson | |
| 6,632,848 B2 | 10/2003 | Sugaya | |
| 6,645,272 B2 | 11/2003 | Lemaire et al. | |
| 6,716,888 B2 | 4/2004 | Bernatowicz et al. | |
| 6,755,892 B2 | 6/2004 | Nalette et al. | |
| 6,814,021 B1 | 11/2004 | Turkewitz et al. | |
| 6,830,596 B1 * | 12/2004 | Deckman | B01J 8/009 422/202 |
| 6,863,713 B1 | 3/2005 | Ghosal et al. | |
| 6,890,497 B2 | 5/2005 | Rau et al. | |
| 6,908,497 B1 | 6/2005 | Sirwardane | |
| 6,969,466 B1 | 11/2005 | Starner | |
| 7,067,456 B2 | 6/2006 | Fan et al. | |
| 7,132,090 B2 | 11/2006 | Dziedzic et al. | |
| 7,270,796 B2 | 9/2007 | Kemp et al. | |
| 7,311,836 B2 * | 12/2007 | Kusunose | B01D 15/163 210/635 |
| 7,343,341 B2 | 3/2008 | Sandor et al. | |
| 7,364,608 B2 | 4/2008 | Tanahashi et al. | |
| 7,384,621 B2 | 6/2008 | Stevens et al. | |
| 7,415,418 B2 | 8/2008 | Zimmerman | |
| 7,420,004 B2 | 9/2008 | Hardy et al. | |
| 7,604,787 B2 | 10/2009 | Maroto-Valer et al. | |
| 7,655,069 B2 | 2/2010 | Wright et al. | |
| 7,699,909 B2 | 4/2010 | Lackner et al. | |
| 7,708,806 B2 | 5/2010 | Wright et al. | |
| 7,776,296 B2 | 8/2010 | Sarlis | |
| 7,795,175 B2 | 9/2010 | Olah et al. | |
| 7,833,328 B2 | 11/2010 | Lackner et al. | |
| 7,993,432 B2 | 8/2011 | Wright et al. | |
| 8,083,836 B2 | 12/2011 | Wright et al. | |
| 8,088,197 B2 | 1/2012 | Wright et al. | |
| 8,133,305 B2 | 3/2012 | Lackner et al. | |
| 8,221,527 B1 | 7/2012 | Wright et al. | |
| 8,246,723 B2 | 8/2012 | Wright et al. | |
| 8,262,774 B2 | 9/2012 | Liu | |
| 8,273,160 B2 | 9/2012 | Wright et al. | |
| 8,337,589 B2 | 12/2012 | Wright et al. | |
| 8,702,847 B2 | 4/2014 | Lackner et al. | |
| 8,715,393 B2 | 5/2014 | Wright et al. | |
| 8,999,279 B2 | 4/2015 | Wright et al. | |
| 9,205,372 B2 | 12/2015 | Wright et al. | |
| 9,266,051 B2 | 2/2016 | Wright et al. | |
| 9,266,052 B2 | 2/2016 | Wright et al. | |
| 9,527,747 B2 | 12/2016 | Wright et al. | |
| 2001/0004895 A1 | 6/2001 | Preiss | |
| 2001/0009124 A1 | 7/2001 | Suzuki et al. | |
| 2001/0022952 A1 | 9/2001 | Rau et al. | |
| 2002/0083833 A1 | 7/2002 | Nalette et al. | |
| 2002/0102674 A1 * | 8/2002 | Anderson | A61F 2/14 435/174 |
| 2002/0178925 A1 | 12/2002 | Mimura et al. | |
| 2003/0022948 A1 | 1/2003 | Seiki et al. | |
| 2003/0024686 A1 | 2/2003 | Ouellette | |
| 2003/0041733 A1 | 3/2003 | Seguin et al. | |
| 2003/0145726 A1 | 8/2003 | Gueret et al. | |

(56) References Cited

U.S. PATENT DOCUMENTS

| | | | |
|---|---|---|---|
| 2003/0167692 A1 | 9/2003 | Jewell et al. | |
| 2003/0205692 A1 | 11/2003 | Fleming et al. | |
| 2003/0220188 A1 | 11/2003 | Marand et al. | |
| 2004/0031424 A1* | 2/2004 | Pope | C10J 3/06 110/230 |
| 2004/0069144 A1 | 4/2004 | Wegeng et al. | |
| 2004/0103831 A1* | 6/2004 | Pope | C10J 3/06 110/341 |
| 2004/0134353 A1 | 7/2004 | Gillingham et al. | |
| 2004/0195115 A1 | 10/2004 | Colombo | |
| 2004/0213705 A1 | 10/2004 | Blencoe et al. | |
| 2004/0219090 A1 | 11/2004 | Dziedzic et al. | |
| 2005/0011770 A1 | 1/2005 | Katsuyoshi et al. | |
| 2005/0063956 A1 | 3/2005 | Bernklau et al. | |
| 2005/0092176 A1* | 5/2005 | Ding | B01D 53/02 95/90 |
| 2005/0095486 A1 | 5/2005 | Hamamoto et al. | |
| 2005/0203327 A1 | 9/2005 | Jovanovic et al. | |
| 2005/0204915 A1 | 9/2005 | Sammons et al. | |
| 2005/0252215 A1* | 11/2005 | Beaumont | A01G 7/02 60/753 |
| 2005/0269094 A1 | 12/2005 | Harris et al. | |
| 2005/0279095 A1* | 12/2005 | Goldman | F01K 13/00 60/641.8 |
| 2006/0013963 A1 | 1/2006 | Thomson | |
| 2006/0042209 A1 | 3/2006 | Dallas et al. | |
| 2006/0051274 A1 | 3/2006 | Wright et al. | |
| 2006/0150811 A1 | 7/2006 | Callahan et al. | |
| 2006/0186562 A1 | 8/2006 | Wright et al. | |
| 2006/0249020 A1 | 11/2006 | Tonkovich et al. | |
| 2006/0289003 A1 | 12/2006 | Lackner et al. | |
| 2007/0004023 A1 | 1/2007 | Trachtenberg | |
| 2007/0089605 A1 | 4/2007 | Lampinen | |
| 2007/0149398 A1 | 6/2007 | Jones et al. | |
| 2007/0187247 A1 | 8/2007 | Lackner et al. | |
| 2007/0199448 A1 | 8/2007 | Yates et al. | |
| 2007/0217982 A1 | 9/2007 | Wright et al. | |
| 2008/0008793 A1 | 1/2008 | Forsyth et al. | |
| 2008/0025893 A1 | 1/2008 | Asprion et al. | |
| 2008/0031801 A1 | 2/2008 | Lackner et al. | |
| 2008/0087165 A1 | 4/2008 | Wright et al. | |
| 2008/0276804 A1 | 11/2008 | Sayari et al. | |
| 2008/0293976 A1 | 11/2008 | Olah et al. | |
| 2009/0120288 A1 | 5/2009 | Lackner et al. | |
| 2009/0130321 A1 | 5/2009 | Liu | |
| 2009/0169452 A1 | 7/2009 | Constantz et al. | |
| 2009/0232861 A1 | 9/2009 | Wright et al. | |
| 2009/0294366 A1* | 12/2009 | Wright | B01D 53/02 210/683 |
| 2009/0320688 A1 | 12/2009 | Lackner et al. | |
| 2010/0095842 A1 | 4/2010 | Lackner et al. | |
| 2010/0105126 A1 | 4/2010 | Wright et al. | |
| 2010/0116137 A1 | 5/2010 | Wright et al. | |
| 2010/0319537 A1 | 12/2010 | Eisenberger et al. | |
| 2011/0027157 A1 | 2/2011 | Wright et al. | |
| 2011/0033357 A1 | 2/2011 | Wright et al. | |
| 2011/0033358 A1 | 2/2011 | Wright et al. | |
| 2011/0056382 A1 | 3/2011 | Lackner et al. | |
| 2011/0079144 A1 | 4/2011 | Wright et al. | |
| 2011/0079146 A1 | 4/2011 | Wright et al. | |
| 2011/0079147 A1 | 4/2011 | Wright et al. | |
| 2011/0081709 A1 | 4/2011 | Wright et al. | |
| 2011/0081710 A1 | 4/2011 | Wright et al. | |
| 2011/0081712 A1 | 4/2011 | Wright et al. | |
| 2011/0083554 A1 | 4/2011 | Wright et al. | |
| 2011/0108421 A1 | 5/2011 | Lackner et al. | |
| 2011/0185897 A1 | 8/2011 | Wright et al. | |
| 2011/0189075 A1 | 8/2011 | Wright et al. | |
| 2011/0203174 A1 | 8/2011 | Lackner | |
| 2011/0203311 A1 | 8/2011 | Wright et al. | |
| 2011/0206588 A1 | 8/2011 | Lackner | |
| 2011/0209614 A1 | 9/2011 | Wright et al. | |
| 2011/0293503 A1 | 12/2011 | Wright et al. | |
| 2012/0058032 A1 | 3/2012 | Lackner et al. | |
| 2012/0220019 A1 | 8/2012 | Lackner | |
| 2012/0279397 A1 | 11/2012 | Wright et al. | |
| 2012/0302469 A1 | 11/2012 | Lackner et al. | |
| 2012/0304858 A1 | 12/2012 | Wright et al. | |
| 2013/0115153 A1 | 5/2013 | Lackner et al. | |
| 2013/0309756 A1 | 11/2013 | Wright et al. | |
| 2013/0336722 A1 | 12/2013 | Wright et al. | |
| 2013/0343981 A1 | 12/2013 | Wright et al. | |
| 2014/0370576 A1 | 12/2014 | Wright et al. | |
| 2015/0020683 A1 | 1/2015 | Wright et al. | |
| 2015/0104554 A1 | 4/2015 | Wright et al. | |
| 2015/0165373 A1 | 6/2015 | Lackner | |
| 2017/0007957 A1 | 1/2017 | Wright et al. | |
| 2017/0043333 A1 | 2/2017 | Wright et al. | |

FOREIGN PATENT DOCUMENTS

| | | |
|---|---|---|
| CN | 1107078 A | 8/1995 |
| CN | 1391642 A | 1/2003 |
| DE | 4130837 A1 | 4/1992 |
| DE | 19521678 A1 | 12/1996 |
| DE | 19727295 A1 | 1/1999 |
| DE | 19830470 C1 | 11/1999 |
| DE | 20001385 U1 | 8/2000 |
| EP | 0020055 A1 | 12/1980 |
| EP | 0111911 A1 | 6/1984 |
| EP | 0254137 A1 | 1/1988 |
| EP | 0585898 A1 | 3/1994 |
| FR | 2029424 A1 | 10/1970 |
| GB | 1004046 A | 9/1965 |
| GB | 1031799 A | 6/1966 |
| GB | 1109439 A | 4/1968 |
| GB | 1204781 A | 9/1970 |
| GB | 1296889 A | 11/1972 |
| GB | 1520110 A | 8/1978 |
| GB | 2288143 A | 10/1995 |
| JP | S58122022 A | 7/1983 |
| JP | S6172035 A | 4/1986 |
| JP | S61227822 A | 10/1986 |
| JP | S61254220 A | 11/1986 |
| JP | S61254221 A | 11/1986 |
| JP | S61280217 A | 12/1986 |
| JP | S6312323 A | 1/1988 |
| JP | S6312324 A | 1/1988 |
| JP | S6316032 A | 1/1988 |
| JP | S6369525 A | 3/1988 |
| JP | S6369527 A | 3/1988 |
| JP | H01208310 A | 8/1989 |
| JP | H01305809 A | 12/1989 |
| JP | H02187153 A | 7/1990 |
| JP | H03245811 A | 11/1991 |
| JP | H04171021 A | 6/1992 |
| JP | H04200720 A | 7/1992 |
| JP | H0557182 A | 3/1993 |
| JP | H0671137 A | 3/1994 |
| JP | H06253682 A | 9/1994 |
| JP | H09276648 A | 10/1997 |
| JP | H1057745 A | 3/1998 |
| JP | 2000051634 A | 2/2000 |
| JP | 2000107895 A | 4/2000 |
| JP | 2004089770 A | 3/2004 |
| JP | 2004261757 A | 9/2004 |
| JP | 2006102561 A | 4/2006 |
| JP | 2006103974 A | 4/2006 |
| JP | 2006266583 A | 10/2006 |
| JP | 2006340683 A | 12/2006 |
| JP | 2007190529 A | 8/2007 |
| JP | 2008116193 A | 5/2008 |
| JP | 2010505613 A | 2/2010 |
| JP | 2011516107 A | 5/2011 |
| KR | 20030012224 A | 2/2003 |
| RU | 1828406 A3 | 7/1993 |
| RU | 2097115 C1 | 11/1997 |
| SU | 511963 A | 4/1976 |
| SU | 715120 A1 | 2/1980 |
| WO | WO-9413386 A1 | 6/1994 |
| WO | WO-9816296 A1 | 4/1998 |
| WO | WO-9817388 A1 | 4/1998 |
| WO | WO-9822173 A1 | 5/1998 |

(56) References Cited

FOREIGN PATENT DOCUMENTS

| WO | WO-0050154 A1 | 8/2000 |
|---|---|---|
| WO | WO-0076633 A1 | 12/2000 |
| WO | WO-0121269 A2 | 3/2001 |
| WO | WO-0151550 A1 | 7/2001 |
| WO | WO-0121269 A3 | 8/2001 |
| WO | WO-2005108297 A2 | 11/2005 |
| WO | WO-2005108297 A3 | 1/2006 |
| WO | WO-2006009600 A2 | 1/2006 |
| WO | WO-2006009600 A3 | 4/2006 |
| WO | WO-2006036396 A2 | 4/2006 |
| WO | WO-2006036396 A3 | 8/2006 |
| WO | WO-2006084008 A1 | 8/2006 |
| WO | WO-2007016271 A2 | 2/2007 |
| WO | WO-2007016274 A2 | 2/2007 |
| WO | WO-2007016271 A3 | 3/2007 |
| WO | WO-2007016274 A3 | 3/2007 |
| WO | WO-2007114991 A2 | 10/2007 |
| WO | WO-2007114991 A3 | 4/2008 |
| WO | WO-2008042919 A2 | 4/2008 |
| WO | WO-2008061210 A2 | 5/2008 |
| WO | WO-2008061210 A3 | 7/2008 |
| WO | WO-2008131132 A1 | 10/2008 |
| WO | WO-2009149292 A1 | 12/2009 |
| WO | WO-2008042919 A3 | 7/2010 |

OTHER PUBLICATIONS

Abandoned U.S. Appl. No. 14/542,120, filed Nov. 14, 2014.
Abandoned U.S. Appl. No. 14/621,931, filed Feb. 13, 2015.
Abandoned U.S. Appl. No. 14/843,700, filed Sep. 2, 2015.
Abandoned U.S. Appl. No. 14/873,484, filed Oct. 2, 2015.
Abandoned U.S. Appl. No. 14/986,830, filed Jan. 4, 2016.
Office action dated Jul. 12, 2017 for U.S. Appl. No. 15/046,621.
Abstracts of Eos. Trans. Agu, 82 (47), Fall Meeting 2001; pp. 3.
Abstracts of Eos. Trans. Agu, 83 (19), Spring Meeting 2002; pp. 3.
Abstracts of Eos. Trans. Agu, 83 (47), Fall Meeting 2002; pp. 3.
Astarita. Mass Transfer with Chemical Reaction. Amsterdam: Elsevier Publishing Company. 1967; 144-152.
Avgul, et al. Adsorption of acid gases by macroporous, weekly basic anion exchange resins with different functional groups. Colloid Journal of the USSR. A translation of Kolloidnyi Zhurnal. 1982; 43(6):837-842.
Balster et al. Multi-Layer Spacer Geometries With Improved Mass Transport. Journal of membrane Science. 2006; 282:351-361.
Belyakova, et al. Adsorption of carbon dioxide and water by macroporous anion-exchange resins. Colloid Journal of the USSR. A translation of Kolloidnyi Zhurnal. 1975; 37(3):484-487.
Besra, et al. Particle Characteristics and Their Influence on Dewatering of Kaolin, Calcite and Quartz Suspensions. Int. J. Miner. Process. 2000; 59:89-122.
Bituin. New Findings May Redefine Renewable Energy Debate. Access Jun. 29, 2009. found at http://www.dailycal.org/article.php?id=8559.
Blok, et al. Hydrogen Production From Natural Gas, Sequestration of Recovered CO2 in Depleted Gas Wells and Enhanced Natural Gas Recovery. Energy. 1997; 22(2-3):161-168.
Boynton. Chemistry and Technology of Lime and Limestone. New York: Interscience Publishers. 1966; 204-206.
Canadian Official Action dated Jun. 21, 2011, Appln. No. 2,577,685.
Carbon Sequestration Could Be Employed Today to Help Alleviate Greenhouse Emissions. Accessed Jun. 29, 2009. found at http://www.earthinstitute.columbia.edu/news/2003/story06-25-03b.html.
Chinese office action dated Dec. 25, 2012 for CN Application 200780036850.5.
Chinese Official Action dated Apr. 28, 2011 Appln. No. 200780042511.8.
Chinese Official Action dated Dec. 3, 2010, Appln. No. 200780008015.
Chinese Official Action dated Jun. 13, 2011, Appln. No. 200780008015.0.
Chinese Official Action dated May 5, 2010 and Jan. 20, 2011, Application No. 200680030297.X.
Choi, et al. A new preparation for cation-exchange membrane using monomer sorption into reinforcing materials. Desalination. Mar. 22, 2002; 146:287-291.
Choi, et al. Characterization of LDPE/polystyrene cation exchange membranes prepared by monomer sorption and UV radiation polymerization. Journal of Membrane Science. 2003; 223:201-215.
Choi, et al. Preparation and characterization of LDPE/polyvinvylbenzyl trimethyl ammonium salts anion-exchange membrane. Journal of Membrane Science. 2003; 2001:219-231.
Co-pending U.S. Appl. No. 15/046,621, filed Feb. 18, 2016.
Co-pending U.S. Appl. No. 15/133,513, filed Apr. 20, 2016.
Cuiming, et al. Fundamental Studies of a New Hybrid (Inorganic-Organic) Positively Charged Membrane: Membrane Preparation and Characterizations. Journal of Membrane Science. 2003; 216:269-278.
Desideri, et al. Performance Modelling of a Carbon Dioxide Removal System for Power Plants. Energy Conversion and Management.1999; 40:1899-1915.
Dillon, et al. Oxy-Combustion Processes for CO2 Capture From Advanced Supercritical PF and NGCC Power Plant. Greenhouse Gas Control Technologies 7, Proceedings of the 7th International Conference on Greenhouse Gas Control Technologies Sep. 5, 2004, Vancouver, Canada. 211-220.
Dow Chemical Company, Dowex Type 1 Strong Base Anion Resin, 1998, http://www.inaqua.de/Prod/ion/pdf en/313 UPCORE Mono A625.pdf, p. 1.
Dubey et al. Chemical Extraction of Carbon Dioxide from Air to Sustain Fossil Energy by Avoiding Climate Change. 2nd Annual Conference on Carbon Sequestration, 2003.
Dubey et al., "Extraction of Carbon Dioxide from the Atmosphere Through Engineered Chemical Sinkage", Fuel Chemistry Division Preprints, 2002; pp. 1-4.
Elliot, et al. Compensation of Atmospheric CO2 Buildup Through Engineered Chemical Sinkage. 2001; pp. 1-8.
European examination report dated Dec. 19, 2011 for EP Application No. 08746144.8.
European office action dated May 9, 2011 for EP Application No. 08746144.8.
European office action dated Jul. 4, 2011 for EP Application No. 07758183.3.
European official action dated Jan. 19, 2010 EP Application No. 05793918.3.
European Official Action, Serial No. 06 788 685.3-1213, dated Oct. 12, 2011 (3 pages).
European search report and opinion dated Jan. 7, 2011 for EP Application No. 07864483.8.
European search report and opinion dated Apr. 20, 2011 for EP Application No. 08746144.8.
European search report and opinion dated Jun. 22, 2010 for EP Application No. 07758183.3.
European search report and opinion dated Jul. 27, 2011 for EP Application No. 07853742.0.
European search report and opinion dated Oct. 16, 2009 for EP Application No. 06788685.3.
European search report and opinion dated Dec. 21, 2011 for EP Application No. 11008476.1.
European search report dated Feb. 28, 2014 for EP Application No. 13175213.1.
European search report partial dated Oct. 11, 2013 for EP Application No. 13175213.1.
Fuertes, et al. Carbon Composite Membranes from Matrimid and Kapton Polymides for Gas Separation. Microporous and Mesoporous Materials. 1999; 33:115-125.
Hanson, et al. Steam Drying and Fluidized-Bed Calcination of Lime Mud. Tappi Journal. 1993; 76(11):181-188.
Hashimoto, et al. Global CO2 recycling. Zairyo to Kankyo/Corrosion Engineering. 1996; 45(10):614-620. (Abstract only).
Hensel. In the Lab. Accessed Jun. 29, 2009. found at www.eponline.comiarticles/53584.
Herzog, et al. Carbon Dioxide Recovery and Disposal From Large Energy Systems. Annu. Rev. Energy Environ. 1996; 21:145-166.

(56) References Cited

OTHER PUBLICATIONS

Huang, et al. Method to Regenerate Ammonia for the Capture of Carbon Dioxide. Energy and Fuels. 2002; 16:904-910.
Information About: David Keith. Access Sep. 26, 2005. found at http://ideas.respec.org/e/pke74.html.
Information on David Keith. Access Jun. 14, 2010. found at http://www.ucalgary.ca/-keith/.
International Preliminary Report on Patentability dated Jan. 16, 2008 for PCT/US2006/003646.
International Preliminary Report on Patentability dated Jan. 29, 2008 for PCT/US2006/029238.
International Preliminary Report on Patentability dated Feb. 15, 2011 for PCT/US2009/053461.
International Preliminary Report on Patentability dated Feb. 20, 2007 for PCT/US2005/029584.
International Preliminary Report on Patentability dated Mar. 3, 2011 for PCT/US2009/054795.
International Preliminary Report on Patentability dated May 11, 2010 for PCT/US2008/082505.
International Preliminary Report on Patentability dated May 25, 2010 for PCT/US2007/084237.
International Preliminary Report on Patentability dated May 28, 2009 for PCT/US2007/084880.
International Preliminary Report on Patentability dated Jun. 1, 2010 for PCT/US2007/80229.
International Preliminary Report on Patentability dated Sep. 9, 2008 for PCT/US2007/063607.
International Preliminary Report on Patentability dated Oct. 20, 2008 for PCT/US2008/060672.
International preliminary report on patentability dated Nov. 7, 2006 for PCT/US2005/015453.
International preliminary report on patentability dated Nov. 7, 2006 for PCT/US2005/015454.
International Preliminary Report on Patentability dated Dec. 6, 2010 for PCT/US2009/046306.
International search report and written opinion dated Nov. 15, 2005 for PCT/US2005/015453.
International search report and written opinion dated Dec. 21, 2005 for PCT/US2005/015454.
International Search report and Written Opinion dated Jan. 27, 2009 for PCT/US2008/084237.
International Search report and Written Opinion dated Jan. 30, 2007 for PCT/US2006/029238.
International Search report and Written Opinion dated Feb. 25, 2008 for PCT/US2007/063607.
International Search report and Written Opinion dated Mar. 6, 2008 for PCT/US2007/080229.
International Search report and Written Opinion dated Apr. 23, 2008 for PCT/US2007/084880.
International search report and written opinion dated May 12, 2009 for PCT/US2009/034554.
International search report and written opinion dated May 21, 2012 for PCT/US2009/053450.
International Search report and Written Opinion dated Jun. 27, 2006 for PCT/US2006/003646.
International search report and written opinion dated Aug. 30, 2007 for PCT/US2005/032848.
International Search report and Written Opinion dated Sep. 3, 2009 for PCT/US2009/046306.
International Search report and Written Opinion dated Sep. 15, 2008 for PCT/US2008/060672.
International Search report and Written Opinion dated Sep. 25, 2009 for PCT/US2009/053461.
International Search Report and Written Opinion dated Oct. 4, 2006 for PCT/US2005/029584.
International search report and written opinion dated Nov. 17, 2010 for PCT/US2010/043133.
International Search report and Written Opinion dated Dec. 9, 2009 for PCT/US2009/054795.
International Search report and Written Opinion dated Dec. 24, 2008 for PCT/US2008/082505.
International Search Report and Written Opinion dated Nov. 24, 2010 GCC/P/2007/9020.
Israel Official Action, Application No. 25585/09, dated Jun. 30, 2011.
Japanese Official Action, Application Serial No. 2008-524154, dated Feb. 16, 2011, 4 pgs.
Japanese Official Action, Application Serial No. 2008-524154, dated May 31, 2011, 3 pgs.
Japanese Official Action, Application Serial No. 2009-531567, dated Feb. 7, 2011, 4 pgs.
Keith et al., "Climate Strategy with CO2 Capture from the Air" 2005; pp. 1-43.
Keith, et al. Co2 Capture From the Air: Technology Assessment and Implications for Climate Policy. Greenhouse Gas Control Technologies 6. Proceedings of the 6th International Conference on Greenhouse Gas Control Technologies Oct. 1-4, 2002, Kyoto, Japan; 187-192.
Keith, et al. CO2 Capture From the Air: Technology Assessment and Implications for Climate Policy. pp. 1-6.
Keith. The Carrot or the Stick: How to Build a Technology-Friendly Climate Policy in Canada. Climate Change Central Apr. 15, 2005, pp. 1-32.
Konno, et al. Crystallization of Aragonite in the Causticizing Reaction. Powder Technology. 2002; 123:33-39.
Korean office action dated Nov. 20, 2012 for KR Application 10-2008-7004729.
Lackner. Can Fossil Carbon Fuel the 21st Century? International Geology Review. 2002; 44:1122-1133.
Lackner, et al., "Capturing Carbon Dioxide From Air". First National Conference on Carbon Sequestrian. 2001; pp. 1-15.
Lackner, et al. Carbon Dioxide Extraction from Air? Arguments 2001.pp. 1-5.
Lackner, et al. Carbon Dioxide Extraction from Air: Is It an Option?. Proceedings of the 24th Annual Technical Conference on Coal Utilization and Fuel Systems, 1999; pp. 885-896.
Lackner et al., "CO2 Extraction from Air" A White Paper from Los Alamos National Labs, The Reddy Corporation International, Sourcebook, Sep. 1999.
Lackner, et al. Free-Market Approaches to Controlling Carbon Dioxide Emissions to the Atmosphere: A Discussion of the scientific basis. Los Alamos National Laboratory (Lackner & Ziock) & Harvard University (Wilson), pp. 1-16.
Lackner, et al. The Case for Carbon Dioxide Extraction From Air. Sourcebook, Sep. 1999; vol. 57, No. 9, pp. 6-10.
Lackner. Extraction CO2 from the Air, Lackner presentation, 12 pages.
Liang, "Carbon Dioxide Capture From Flue Gas Using Regenerable Sodium-Based Sorbents", dated Aug. 1, 2003, Department of Chemical Engineering Thesis, (137 pgs).
Liu, et al. Composite Membranes from Photochemical Synthesis of Ultrathin Polymer Films. Nature vol. 352 Jul. 4, 1991.
Meier, et al. Design and Experimental Investigation of a Horizontal Rotary Reactor for the Solar Thermal Production of Lime. Energy. 2004; 29:811-821.
Mexican office action dated Oct. 29, 2012 for MX/a/2008/001054.
Mexican Official Action, dated Feb. 2, 2011, Serial No. MX/a/2008/011464.
Mexican Official Action, dated Jan. 24, 2011, Serial No. MX/a/2007/002019.
Mexican Official Action, Serial No. MX/a/2007/002019, dated Aug. 31, 2011 (Mexico Attorney notified Attorney of record in instant application on Sep. 22, 2011) (2 pages).
Mexican Official Action, Serial No. MX/a/2009/003500, dated Oct. 12, 2011 (3 pages).
Mizutani. Structure of Ion Exchange Membranes. Journal of Membrane Science. 1990; 49:121-144.89.
Murdoch, et al. Sabatier Methanation Reactor for Space Exploration. (2005) A Collection of Technical Papers—1st Space Exploration Conference: Continuing the Voyage of Discovery, 2, pp. 981-987 (Abstract only).

(56) References Cited

OTHER PUBLICATIONS

Notice of allowance dated Jul. 13, 2015 for U.S. Appl. No. 13/550,691.
Notice of allowance dated Aug. 10, 2016 for U.S. Appl. No. 14/561,831.
Notice of allowance dated Aug. 25, 2014 for U.S. Appl. No. 13/733,227.
Notice of allowance dated Oct. 6, 2015 for U.S. Appl. No. 14/183,751.
Notice of allowance dated Oct. 15, 2015 for U.S. Appl. No. 13/733,227.
Notice of allowance dated Nov. 30, 2016 for U.S. Appl. No. 14/163,559.
Notice of allowance dated Dec. 22, 2009 for U.S. Appl. No. 11/866,326.
Office action dated Jan. 25, 2011 for U.S. Appl. No. 11/227,660.
Office action dated Jan. 27, 2010 for U.S. Appl. No. 11/227,660.
Office action dated Jan. 28, 2014 for U.S. Appl. No. 13/386,587.
Office action dated Jan. 29, 2014 for U.S. Appl. No. 12/996,589.
Office action dated Jan. 29, 2016 for U.S. Appl. No. 14/444,882.
Office action dated Feb. 1, 2011 for U.S. Appl. No. 11/209,962.
Office action dated Feb. 3, 2012 for U.S. Appl. No. 13/102,915.
Office action dated Feb. 4, 2010 for U.S. Appl. No. 12/555,874.
Office action dated Feb. 11, 2011 for U.S. Appl. No. 12/638,717.
Office action dated Feb. 23, 2010 for U.S. Appl. No. 11/209,962.
Office action dated Feb. 25, 2015 for U.S. Appl. No. 13/550,691.
Office action dated Mar. 6, 2015 for U.S. Appl. No. 13/733,227.
Office action dated Mar. 9, 2009 for U.S. Appl. No. 11/207,236.
Office action dated Mar. 11, 2011 for U.S. Appl. No. 12/903,962.
Office action dated Mar. 11, 2011 for U.S. Appl. No. 12/903,967.
Office action dated Mar. 11, 2011 for U.S. Appl. No. 12/903,970.
Office action dated Mar. 11, 2011 for U.S. Appl. No. 12/903,974.
Office action dated Mar. 11, 2011 for U.S. Appl. No. 12/903,981.
Office action dated Mar. 14, 2012 for U.S. Appl. No. 11/209,962.
Office action dated Mar. 15, 2010 for U.S. Appl. No. 11/683,824.
Office action dated Mar. 18, 2016 for U.S. Appl. No. 13/058,812.
Office action dated Mar. 21, 2016 for U.S. Appl. No. 14/163,559.
Office action dated Mar. 28, 2011 for U.S. Appl. No. 12/389,213.
Office action dated Mar. 30, 2009 for U.S. Appl. No. 11/346,522.
Office action dated Apr. 6, 2011 for U.S. Appl. No. 11/996,615.
Office action dated Apr. 13, 2012 for U.S. Appl. No. 13/102,901.
Office action dated Apr. 20, 2015 for U.S. Appl. No. 14/183,751.
Office action dated May 4, 2012 for U.S. Appl. No. 13/295,950.
Office action dated May 26, 2011 for U.S. Appl. No. 11/209,962.
Office action dated Jun. 9, 2010 for U.S. Appl. No. 11/209,962.
Office action dated Jun. 17, 2009 for U.S. Appl. No. 11/346,522.
Office action dated Jun. 26, 2014 for U.S. Appl. No. 13/733,227.
Office action dated Jun. 28, 2010 for U.S. Appl. No. 11/683,824.
Office action dated Jul. 1, 2011 for U.S. Appl. No. 13/102,915.
Office action dated Jul. 3, 2008 for U.S. Appl. No. 11/207,236.
Office action dated Jul. 3, 2012 for U.S. Appl. No. 13/102,901.
Office action dated Jul. 16, 2012 for U.S. Appl. No. 12/389,213.
Office action dated Aug. 1, 2011 for U.S. Appl. No. 12/903,974.
Office action dated Aug. 1, 2012 for U.S. Appl. No. 12/903,877.
Office action dated Aug. 3, 2011 for U.S. Appl. No. 12/903,962.
Office action dated Aug. 3, 2012 for U.S. Appl. No. 12/903,953.
Office action dated Aug. 3, 2016 for U.S. Appl. No. 14/163,559.
Office action dated Aug. 7, 2014 for U.S. Appl. No. 13/557,701.
Office action dated Aug. 8, 2012 for U.S. Appl. No. 12/903,873.
Office action dated Aug. 9, 2012 for U.S. Appl. No. 12/903,894.
Office action dated Aug. 10, 2012 for U.S. Appl. No. 12/903,886.
Office action dated Aug. 10, 2015 for U.S. Appl. No. 14/163,559.
Office action dated Aug. 11, 2015 for U.S. Appl. No. 13/733,227.
Office action dated Aug. 13, 2012 for U.S. Appl. No. 12/903,898.
Office action dated Aug. 15, 2014 for U.S. Appl. No. 13/550,691.
Office action dated Aug. 27, 2010 for U.S. Appl. No. 11/209,962.
Office action dated Aug. 28, 2012 for U.S. Appl. No. 12/903,868.
Office action dated Aug. 30, 2012 for U.S. Appl. No. 12/903,958.
Office action dated Aug. 30, 2013 for U.S. Appl. No. 13/796,855.
Office action dated Sep. 10, 2012 for U.S. Appl. No. 13/058,802.
Office action dated Sep. 11, 2009 for U.S. Appl. No. 11/209,962.
Office action dated Sep. 27, 2011 for U.S. Appl. No. 12/389,213.
Office action dated Sep. 27, 2011 for U.S. Appl. No. 13/102,915.
Office action dated Sep. 29, 2011 for U.S. Appl. No. 12/615,971.
Office action dated Oct. 1, 2009 for U.S. Appl. No. 11/227,660.
Office action dated Oct. 7, 2009 for U.S. Appl. No. 11/683,824.
Office action dated Oct. 7, 2010 for U.S. Appl. No. 11/227,660.
Office action dated Oct. 24, 2013 for U.S. Appl. No. 13/737,818.
Office action dated Nov. 3, 2011 for U.S. Appl. No. 12/274,986.
Office action dated Nov. 3, 2016 for U.S. Appl. No. 13/058,812.
Office action dated Nov. 9, 2010 for U.S. Appl. No. 12/638,717.
Office action dated Nov. 9, 2012 for U.S. Appl. No. 13/045,317.
Office action dated Nov. 10, 2010 for U.S. Appl. No. 11/996,615.
Office action dated Nov. 19, 2010 for U.S. Appl. No. 11/683,824.
Office action dated Dec. 1, 2011 for U.S. Appl. No. 13/102,901.
Office action dated Dec. 3, 2013 for U.S. Appl. No. 13/557,701.
Office action dated Dec. 7, 2012 for U.S. Appl. No. 13/295,950.
Office action dated Dec. 8, 2015 for U.S. Appl. No. 14/561,831.
Office action dated Dec. 9, 2013 for U.S. Appl. No. 13/550,691.
Office action dated Dec. 12, 2013 for U.S. Appl. No. 13/733,227.
Office action dated Dec. 18, 2014 for U.S. Appl. No. 13/058,812.
Office action dated Dec. 20, 2012 for U.S. Appl. No. 11/209,962.
Official Action issued in Applicants' counterpart Chinese Patent Application Serial No. 200680003905.8 dated Jun. 12, 2009.
Official Action issued in Applicants' counterpart Russian Patent Application Serial No. 2008139902 dated Feb. 4, 2011.
Official Action issued in Applicants' counterpart Russian Patent Application Serial No. 2008139902 dated Nov. 19, 2010.
Official Action issued in Applicants' counterpart Russian Patent Application Serial No. 2009116621/05 dated Jun. 1, 2011.
Official Action received in Applicants' related Australian Patent Application Serial No. 2005290082 dated Apr. 13, 2010.
Official Action received in Applicants' related Australian Patent Application Serial No. 2005290082 dated Apr. 20, 2007.
Official Action received in Applicants' related Australian Patent Application Serial No. 2005290082 dated Jul. 22, 2010.
Official Action received in Applicants' related Australian Patent Application Serial No. 2005290082 dated Mar. 5, 2010.
Official Action received in Applicants' related Australian Patent Application Serial No. 2005290082 dated May 20, 2010.
Official Action received in Applicants' related Australian Patent Application Serial No. 2007233275 dated Jan. 14, 2011.
Official Action received in Applicants' related Australian Patent Application Serial No. 2007233275 dated Jun. 1, 2011.
Official Action received in Applicants' related Australian Patent Application Serial No. 2007303240 dated Feb. 9, 2011.
Official Action received in Applicants' related Australian Patent Application Serial No. 2007319211 dated Jun. 17, 2011.
Official Action received in Applicants' related Australian Patent Application Serial No. 2010241388 dated Jul. 7, 2011.
Official Action received in Applicants' related Mexican Patent Application Serial No. MX/a/2007/009081, dated Jul. 18, 2011.
Official Action received in Applicants' related New Zealand Patent Application Serial No. 575870 dated Jun. 27, 2011.
Official Action received in Applicants' related New Zealand Patent Application Serial No. 575870 dated Mar. 17, 2011 and Nov. 11, 2010.
Official Action received in related Australian Patent Application Serial No. 2006210619 dated Mar. 1, 2010.
Olsson, et al. Thermophysical Properties of Aqueous NaOH-H20 Solutions at High Concentrations. International Journal of Thermophysics. 1997; 18(3)179-793.
Otsuji, et al. A regenerable carbon dioxide removal and oxygen recovery system for the Japanese Experiment Module. Acta Astronaut. Jan. 1987;15(1):45-54.
Researchers Explore Extracting CO2 Directly From Air. Apr. 15, 2002. found at http://www.earthvision.net/ColdFusion/News Page1.cfm?NewsID=20309.
Resume of David Keith, Academic CV, Spring 2005, 8 pgs.
Rickman. Imagine No Restriction on Fossil-Fuel Usage and No Global Warming! Accessed Jun. 29, 2009. found at http://www.lanl.govinews/releases/archive/02-028.shtml.

(56) References Cited

OTHER PUBLICATIONS

Russian office action dated Jan. 5, 2013 for RU Application 2008139902.
Russian Official Action + Translation, dated Feb. 11, 2010, Appin. No. 2007132880/15, (13 pgs).
Russian Official Action + Translation, dated Feb. 2, 2006, Appin. No. 2007132880/15.
Russian Official Action + Translation, dated Sep. 15, 2010 Appin. No. 2007132880/15.
Russian Official Action, Serial No. 2008139902/15, dated Jul. 20, 2011 (Russian Attorney notified Attorney of record in instant application on Sep. 15, 2011) (6 pages).
Russian Official Action, Serial No. 200914222/05, dated Sep. 30, 2011 (9 pages).
Sata, et al. Modification of Properties of Ion Exchange Membranes. VI. Electrodialytic Transport Properties of Cation Exchange Membranes with a Electrodeposition Layer of Cationic Polyelectrolytes. 1979, pp. 1199-1213.
Sata, et al. Modification of Properties of Ion Exchange Membranes. VII. Relative Transport Number between Various Cations of Cation Exchange Membrane Having Cationic Polyelectrolyte Layer and Mechanism of Selective Permeation of Particular Cations. 1979, pp. 2071-2085.
Sata. Modification of Properties of Ion Exchange Membranes. IV. Change of Transport Properties of Cation-Exchange Membranes by Various Polyelectrolytes. 1978, pp. 1063-1080.
Sata. Monovalent Cation Permselective Exchange Membrane. Apr. 15, 1972, pp. 980-982.
Singer. Americans Believe in Global Warming . . . and Psychic Powers, Astrology, and UFO's. Accessed Jun. 29, 2009. Environment & Climate News, 2002; vol. 5, No. 7. found at http://heartland.org/.
Singh. Technical Note Ultrasonically Assisted Rapid Solid-Liquid Separation of Fine Clean Coal Particles. Minerals Engineering. 1999; 12(4):437-443.
Snowpure, LLC, SnowPure Excellion Product Information and Brochure. Aug. 2009.
Steinberg, et al. Synthetic carbonaceous fuel and feedstock using nuclear power, air and water. International Journal of Hydrogen Energy. 1977; 2:189-207.
Strieber. New Solutions to Oil Problems, Whitley Strieber's Unknown Country, 2002, found at http://www.unknowncountry.com/news/print.phtml?id=1467.
Sun et al., "$CO_2$ sorption in activated carbon in the presence of water", dated Feb. 9, 2007, Science Direct, Chemical Physics Letterse 437 (2000) (abstract enclosed).
U.S. Appl. No. 14/163,559, filed Jan. 24, 2014.
U.S. Appl. No. 14/257,698, filed Apr. 21, 2014.
U.S. Appl. No. 14/444,882, filed Jul. 28, 2014.
U.S. Appl. No. 14/542,120, filed Nov. 14, 2014.
U.S. Appl. No. 14/561,831, filed Dec. 5, 2014.
U.S. Appl. No. 14/621,931, filed Feb. 13, 2015.
U.S. Notice of Allowance, U.S. Appl. No. 12/265,556, dated Nov. 7, 2011 (33 pages).
U.S. Official Action, U.S. Appl. No. 11/209,962, dated Oct. 6, 2011 (24 pages).
U.S. Official Action, U.S. Appl. No. 13/208,156, dated Oct. 26, 2011 (21 pages).
Weber, et al. The absorption of carbon dioxide by weak base ion exchange resins. Aiche Journal. Jul. 1970; 609-614. http://onlinelibrary.wiley.com/doi/10.1002/aic.690160417/pdf.
Weimer, et al. $CO_2$ removal and fixation solar high temperature syngas generation for fuel synthesis. Energy Conyers. Mgmt. 1997; 38:S379-S384.
White, et al. Separation and capture of $CO_2$ from large stationary sources and sequestration in geological formations—coalbeds and deep saline aquifers. J Air Waste Manag Assoc. Jun. 2003;53(6):645-715.
Written Public Comments on the Strategic Plan for the U.S. Climate Change Science Program, General Comments. 2003, pp. 1-160.
Yin, et al., "Absorption and steam desorption performance of weak base anion exchange resin" (1995) Hangtian Yixue Yu Yixue Gongcheng/Space Medicine and Medical Engineering, 8 (1), pp. 27-31. (Abstract only).
Zeman, et al. Capturing carbon dioxide directly from the atmosphere. World resource review. 2004; 16(2):157-172.
Zsako, et al Use of Thermal Analysis in the Study of Sodium Carbonate Causticization by Means of Dolomitic Lime. Journal of Thermal Analysis. 1998; 53:323-331.

\* cited by examiner

METHOD AND APPARATUS FOR EXTRACTING CARBON DIOXIDE FROM AIR

CROSS REFERENCE TO RELATED APPLICATIONS

The present application is a Continuation Application which claims the benefit of U.S. application Ser. No. 14/986,830, filed Jan. 4, 2016, which is a Continuation Application of U.S. application Ser. No. 14/183,751, filed Feb. 19, 2014, now U.S. Pat. No. 9,266,052; which is a Continuation Application which claims the benefit of U.S. application Ser. No. 13/796,855, filed Mar. 12, 2013, now abandoned; which is a Continuation Application which claims the benefit of U.S. application Ser. No. 12/903,958, filed Oct. 13, 2010, now abandoned; which is a Continuation Application which claims the benefit of U.S. application Ser. No. 12/638,717, filed Dec. 15, 2009, now abandoned; which is a Divisional Application which claims the benefit of U.S. application Ser. No. 11/866,326, filed Oct. 2, 2007, now U.S. Pat. No. 7,708,806; which claims priority from U.S. Provisional Application Ser. No. 60/827,849, filed Oct. 2, 2006, and 60/829,376, filed Oct. 13, 2006, the contents of which are incorporated herein by reference.

FIELD OF THE INVENTION

The present invention in one aspect relates to removal of selected gases from air. The invention has particular utility for the extraction and sequestration of carbon dioxide ($CO_2$) from air and will be described in connection with such utilities, although other utilities are contemplated.

BACKGROUND OF THE INVENTION

There is compelling evidence to suggest that there is a strong correlation between the sharply increasing levels of atmospheric $CO_2$ with a commensurate increase in global surface temperatures. This effect is commonly known as Global Warming. Of the various sources of the $CO_2$ emissions, there are a vast number of small, widely distributed emitters that are impractical to mitigate at the source. Additionally, large scale emitters such as hydrocarbon-fueled power plants are not fully protected from exhausting $CO_2$ into the atmosphere. Combined, these major sources, as well as others, have lead to the creation of a sharply increasing rate of atmospheric $CO_2$ concentration. Until all emitters are corrected at their source, other technologies are required to capture the increasing, albeit relatively low, background levels of atmospheric $CO_2$. Efforts are underway to augment existing emissions reducing technologies as well as the development of new and novel techniques for the direct capture of ambient $CO_2$. These efforts require methodologies to manage the resulting concentrated waste streams of $CO_2$ in such a manner as to prevent its reintroduction to the atmosphere.

The production of $CO_2$ occurs in a variety of industrial applications such as the generation of electricity power plants from coal and in the use of hydrocarbons that are typically the main components of fuels that are combusted in combustion devices, such as engines. Exhaust gas discharged from such combustion devices contains $CO_2$ gas, which at present is simply released to the atmosphere. However, as greenhouse gas concerns mount, $CO_2$ emissions from all sources will have to be curtailed. For mobile sources the best option is likely to be the collection of $CO_2$ directly from the air rather than from the mobile combustion device in a car or an airplane. The advantage of removing $CO_2$ from air is that it eliminates the need for storing $CO_2$ on the mobile device.

Extracting carbon dioxide ($CO_2$) from ambient air would make it possible to use carbon-based fuels and deal with the associated greenhouse gas emissions after the fact. Since $CO_2$ is neither poisonous nor harmful in parts per million quantities, but creates environmental problems simply by accumulating in the atmosphere, it is possible to remove $CO_2$ from air in order to compensate for equally sized emissions elsewhere and at different times.

Most prior art methods, however, result in the inefficient capture of $CO_2$ from air because these processes heat or cool the air, or change the pressure of the air by substantial amounts. As a result, the net loss in $CO_2$ is negligible as the cleaning process may introduce $CO_2$ into the atmosphere as a byproduct of the generation of electricity used to power the process.

Various methods and apparatus have been developed for removing $CO_2$ from air. For example, we have recently disclosed methods for efficiently extracting carbon dioxide ($CO_2$) from ambient air using capture solvents that either physically or chemically bind and remove $CO_2$ from the air. A class of practical $CO_2$ capture sorbents include strongly alkaline hydroxide solutions such as, for example, sodium or potassium hydroxide, or a carbonate solution such as, for example, sodium or potassium carbonate brine. See for example published PCT Application PCT/US05/29979 and PCT/US06/029238.

There are also many uses for sequestered $CO_2$. This includes the use of $CO_2$ in greenhouses where higher levels of $CO_2$ contribute to increased plant growth. $CO_2$ may also be supplied to algae cultures. Researchers have shown that algae can remove up to 90% of gaseous $CO_2$ from air streams enriched in $CO_2$ and can also reduce the $CO_2$ concentration in ambient air.

SUMMARY OF THE INVENTION

The present invention provides a system, i.e. a method and apparatus for extracting carbon dioxide ($CO_2$) from ambient air and for delivering that extracted $CO_2$ to controlled environments.

In a first exemplary embodiment, the present invention extracts $CO_2$ from ambient air and delivers the extracted $CO_2$ to a greenhouse. Preferably, the $CO_2$ is extracted from ambient air using a strong base ion exchange resin that has a strong humidity function, that is to say, an ion exchange resin having the ability to take up $CO_2$ as humidity is decreased, and give up $CO_2$ as humidity is increased. Several aspects of this invention can also be used to transfer $CO_2$ from the collector medium into the air space of a greenhouse where the $CO_2$ is again fixed in biomass. In a preferred embodiment of the invention, $CO_2$ is extracted from ambient air using an extractor located adjacent to a greenhouse, and the extracted $CO_2$ is delivered directly to the interior of the greenhouse for enriching the greenhouse air with $CO_2$ in order to promote plant growth.

In a second exemplary embodiment, this invention allows the transfer of $CO_2$ from a collector medium into an algae culture, where the $CO_2$ carbon is fixed in biomass. The algae biomass can then be used for the production of biochemical compounds, fertilizer, soil conditioner, health food, and biofuels to name just a few applications or end-uses.

This invention also discloses transfer of $CO_2$ in gaseous phase and as a bicarbonate ion. In one embodiment, a calcareous algae is used which creates calcium carbonate $CaCO_3$ internally, and precipitates the $CaCO_3$ out as limestone.

Accordingly, in broad concept, the present invention extracts $CO_2$ from ambient air using one of several $CO_2$ extraction techniques as described, for example, in our aforesaid PCT/US05/29979 and PCT/US06/029238. Where a carbonate/bicarbonate solution is employed as the primary $CO_2$ sorbent, the $CO_2$ bearing sorbent may be used directly as a feed to the algae. Where the $CO_2$ is extracted using an ion exchange resin as taught, for example in our aforesaid PCT/US06/029238 application, the $CO_2$ is stripped from the resin using a secondary carbonate/bicarbonate wash which then is employed as a feed to the algae. In a preferred alternative embodiment, the carbonate is fed to the algae in a light enhanced bioreactor.

Thus, the present invention provides a simple, relative low-cost solution that addresses both $CO_2$ capture from ambient air and subsequent disposal of the captured $CO_2$.

BRIEF DESCRIPTION OF THE DRAWINGS

Further features and advantages of the present invention will be seen from the following detailed description, taken in conjunction with the accompanying drawings, wherein.

DETAILED DESCRIPTION OF PREFERRED EMBODIMENTS

Figure 1:
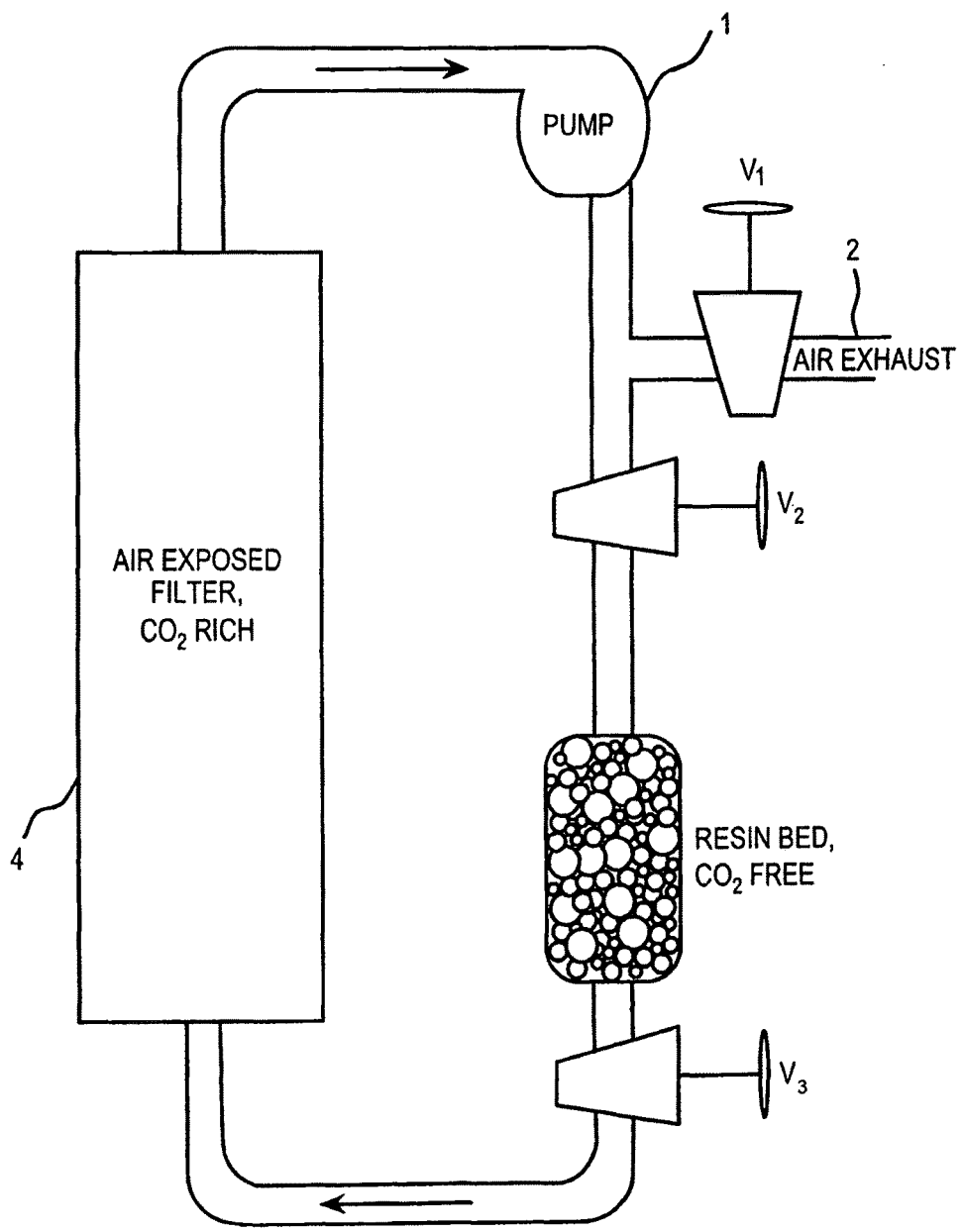
FIG. 1 is a block flow diagram illustrating the use of humidity sensitive ion exchange resins in accordance with the present invention.

In broad concept, the present invention in one aspect extracts carbon dioxide from ambient air using a conventional $CO_2$ extraction method or one of the improved $CO_2$ extraction methods disclosed in our aforesaid PCT Applications, or disclosed herein, and releases at least a portion of the extracted $CO_2$ to a closed environment.

In a first exemplary embodiment, this closed environment is a greenhouse. Preferably, but not necessarily, the $CO_2$ extractor is located adjacent to the greenhouse and, in a preferred embodiment the extractor also provides shading for crops grown in greenhouses which are sensitive to strong sunlight, and/or reduces cooling requirements for the greenhouse.

In one approach to $CO_2$ capture, the resin medium is regenerated by contact with the warm highly humid air. It has been shown that the humidity stimulates the release of $CO_2$ stored on the storage medium and that $CO_2$ concentrations between 3% and 10% can be reached by this method, and in the case of an evacuated/dehydrated system, close to 100% can be reached. In this approach the $CO_2$ is returned to gaseous phase and no liquid media are brought in contact with the collector material.

The $CO_2$ extractor is immediately adjacent to the greenhouse and is moved outside the greenhouse to collect $CO_2$ and moved into the greenhouse to give off $CO_2$. In such embodiment, the $CO_2$ extractor preferably comprises a humidity sensitive ion exchange resin in which the ion exchange resin extracts $CO_2$ when dry, and gives the $CO_2$ up when exposed to higher humidity. A humidity swing may be best suited for use in arid climates. In such environment the extractor is exposed to the hot dry air exterior to the greenhouse, wherein $CO_2$ is extracted from the air. The extractor is then moved into the warm, humid environment of the greenhouse where the ion exchange resin gives up $CO_2$. The entire process may be accomplished without any direct energy input other than the energy to move the extractor from outside to inside the greenhouse and vice versa.

Ion exchange resins are commercially available and are used, for example, for water softening and purification. We have found that certain commercially available ion exchange resins which are humidity sensitive ion exchange resins and comprise strong base resins, advantageously may be used to extract $CO_2$ from the air in accordance with the present invention. With such materials, the lower the humidity, the higher the equilibrium carbon loading on the resin.

Thus, a resin which at high humidity level appears to be loaded with $CO_2$ and is in equilibrium with a particular partial pressure of $CO_2$ will exhale $CO_2$ if the humidity is increased and absorb additional $CO_2$ if the humidity is decreased. The effect is large, and can easily change the equilibrium partial pressure by several hundred and even several thousand ppm. The additional take up or loss of carbon on the resin is also substantial if compared to its total uptake capacity.

There also seems to be an effect on humidity on the transfer coefficient, i.e. the reaction kinetics seem to change with changing humidity. However, the measured flux in and out of the resin seems to depend strongly on the difference between the actual partial pressure and the thermodynamic equilibrium pressure. As the equilibrium pressure changes with humidity, the size of the flux can be affected without an actual change in the reaction kinetics.

In addition, it is possible that kinetics is affected by other issues. For example, ion exchange materials which we have found to be particularly useful, are Anion 1-200 ion exchange membrane materials available from Snowpure LLC, of San Clemente, Calif. The manufacturer describes Anion 1-200 ion exchange membrane material as a strong base, Type 1 functionality ion exchange material. This material, which is believed made according to the U.S. Pat. No. 6,503,957 and is believed to comprise small resin charts encapsulated—or partially encapsulated—in an inactive polymer like polypropylene. We have found that if one first hydrates this material and then dries it, the material becomes porous and readily lets air pass through. The hydration/dehydration preparation is believed to act primarily to swell the polypropylene binder, and has little or no permanent effect on the resin, while the subsequent humidity swings have no observed impact on the polypropylene binder. We have found that these strong base ion exchange resin materials have the ability to extract $CO_2$ from dry air, and give the $CO_2$ out when humidity is raised without any other intervention. The ability of these materials to extract $CO_2$ directly from the air, when dry, and exhale the $CO_2$ as humidity is raised, has not previously been reported.

As noted supra, it is necessary to first hydrate this material and then dry it, before using, whereupon the material becomes porous and readily lets air pass through. Before hydration, the membrane material is substantially non-porous, or at least it is unable to permit passage of an appreciable amount of air through the membrane. However, after hydration and drying, the material is believed to undergo irreversible deformation of the polypropylene matrix during the resin swelling under hydration. Once the material has been deformed, the polypropylene matrix maintains its extended shape even after the resin particles shrink when drying. Thus, for substantially non-porous materials such as the Snowpure Ion Exchange material above described, it is necessary to precondition the material by hydrating and then drying the material before use.

We have observed a large change in the equilibrium partial pressure of $CO_2$ over the resin with a change in humidity. Humidity either changes the state of the resin, or alternatively the entire system that needs to be considered is the $CO_2/H_2O$ resin system. While not wishing to be bound by theory, it is believed that the free energy of binding $CO_2$ to the resin is a function of the $H_2O$ partial pressure with which the resin is in equilibrium.

This makes it possible to have resins absorb or exhale $CO_2$ with a simple swing in humidity without the need to resort to thermal swing and/or pressure swing, which would add to energy costs which could have an unfavorable effect with regard to the overall carbon dioxide balance of the system.

The amount of water involved in such a swing appears to be quite small. The possibility of a humidity swing also allows us to recover $CO_2$ from an air collector with minimal water losses involved.

Other strong base Type 1 and Type 2 functionality ion exchange materials are available commercially from a variety of venders including Dow, DuPont and Rohm and Haas, and also advantageously may be employed in the present invention, either as available from the manufacturer, or formed into heterogeneous ion-exchange membranes following, for example, the teachings of U.S. Pat. No. 6,503, 957.

FIG. 1 illustrates a first embodiment of our invention. A primary ion exchange filter material 4 is provided in a recirculation cycle. A primary pump 1 or a secondary pump (not shown) is used to remove the bulk of the air in the system while valve $V_1$ is open and push it out through the air exhaust 2. At this point valve $V_1$ is closed and a secondary ion exchange capture resin is switched into the system by opening valves $V_2$ and $V_3$. The secondary ion exchange resin can be utilized to provide humidity and possibly some heat. Warm steam stimulates the release of $CO_2$ from the primary ion exchange filter material 4, which is then captured on the secondary ion exchange resin which is still out of equilibrium with the $CO_2$ partial pressure. The volume of water in the system remains small as it is recirculated and not taken up by the secondary resin. While $CO_2$ is unloading from the primary ion exchange resin material 14 and being absorbed by the secondary ion exchange resin, the bulk of the water cycles through the apparatus. The amount of water that can be devolved or absorbed is much smaller than the amount of $CO_2$ that is transferred. At the end of the cycle the primary ion exchange filter material 14 is refreshed and the secondary ion exchange capture resin is loaded with $CO_2$.

This system could be used to transfer $CO_2$ from the air capture medium, e.g. an ion exchange resin onto a secondary resin without washing or wetting the primary resin. This has two advantages. First, the primary resin is not directly exposed to chemicals such as amines that were used in the past and described in our aforesaid PCT Application PCT/US061/029238. Second, we have seen that wet resins are ineffective in absorbing $CO_2$ until they have dried out. It is therefore advantageous to avoid the wetting of the material and thus operate in this fashion where the resin is washed with low-pressure steam. Steam pressures could be less than 100 Pa and thus be saturated at temperatures similar to ambient values. However, the $CO_2$ exchange is obviously accelerated at higher temperatures and higher steam pressures. The disadvantage of raising temperatures would be additional energy consumption.

The design outlined here is a special example of a broader class of designs where the secondary resin is replaced with any other sorbent material that is capable of absorbing $CO_2$ without absorbing water. Such sorbents may include liquid amines, ionic liquids, solid $CO_2$ sorbents such as lithium zirconate, lithium silicate, magnesium hydroxide or calcium hydroxide, or any of a wide class of chemical or physical sorbents capable of absorbing $CO_2$ from a gas mixture including water vapor and $CO_2$. The central concept is that of using a humidity swing, rather than a pressure or temperature swing to remove $CO_2$ from the primary sorbent without bringing it in direct physical contact with a secondary sorbent.

Application in a Greenhouse for Improving Crop Yields

As noted supra, crop yield in greenhouses can be improved by increasing the carbon dioxide level in the greenhouse air. The present invention provides for the introduction of carbon dioxide into a greenhouse without combusting fuels emitting fossil fuel $CO_2$ into the air. More particularly, we have found that we can employ humidity sensitive ion exchange resins to capture $CO_2$ from dry outside air, and then release the $CO_2$ into the greenhouse by exposing the resins to the warm moist greenhouse air.

In greenhouses located in warm in desert climates such as found in the Southwest United States, the outside $CO_2$ loading may be performed at night when outside temperatures are cooler which may enhance $CO_2$ uptake capacity. In cooler climates where greenhouses rely in part on radiative heating, our system of $CO_2$ loading avoids the need to let in cold air to replenish the $CO_2$ and thus reduces the need for heating employing fossil fuel consumption until temperatures drop so low that fuel based heating becomes necessary.

In one embodiment, we employ several filters made from humidity sensitive ion exchange active material. In one part of the cycle the filters are exposed to outside air that could be driven by natural wind flow, by thermal convection, or fans. It is preferable to avoid fans as they add an unnecessary energy penalty. In a second part of the cycle, moist air from inside the greenhouse preferably is driven through the filter material, e.g. by fans, which then releases $CO_2$ into the greenhouse atmosphere. Since the climate control of the greenhouse typically will rely on a fan system anyway, there is little or no energy penalty.

Since plants at night respire, in some greenhouse designs it is possible to strip the $CO_2$ from the greenhouse air by pulling the greenhouse air through the filters. The filters can then be exposed to higher humidity to facilitate the daytime release of the $CO_2$ into the greenhouse.

Figure 2B:
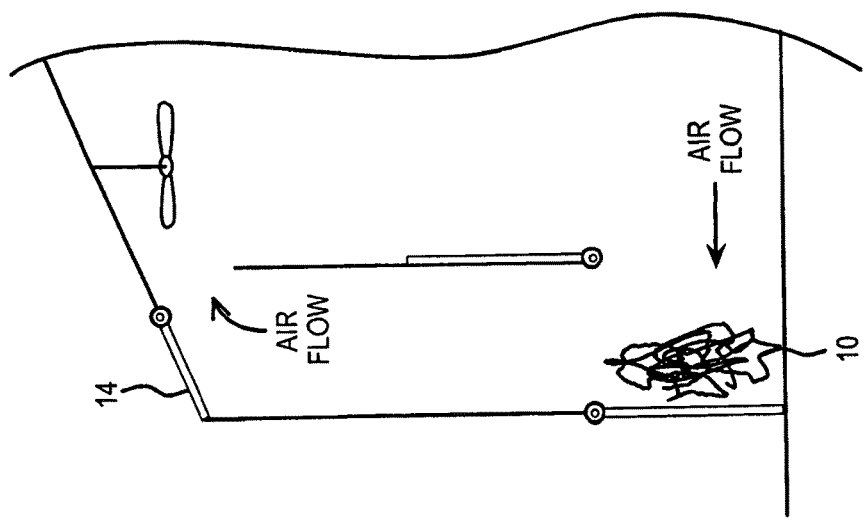
FIGS. 2*a* and 2*b* are schematic views of a $CO_2$ extractor/greenhouse feeder in accordance with the present invention, where filter units are located adjacent an exterior wall.
Figure 2A:
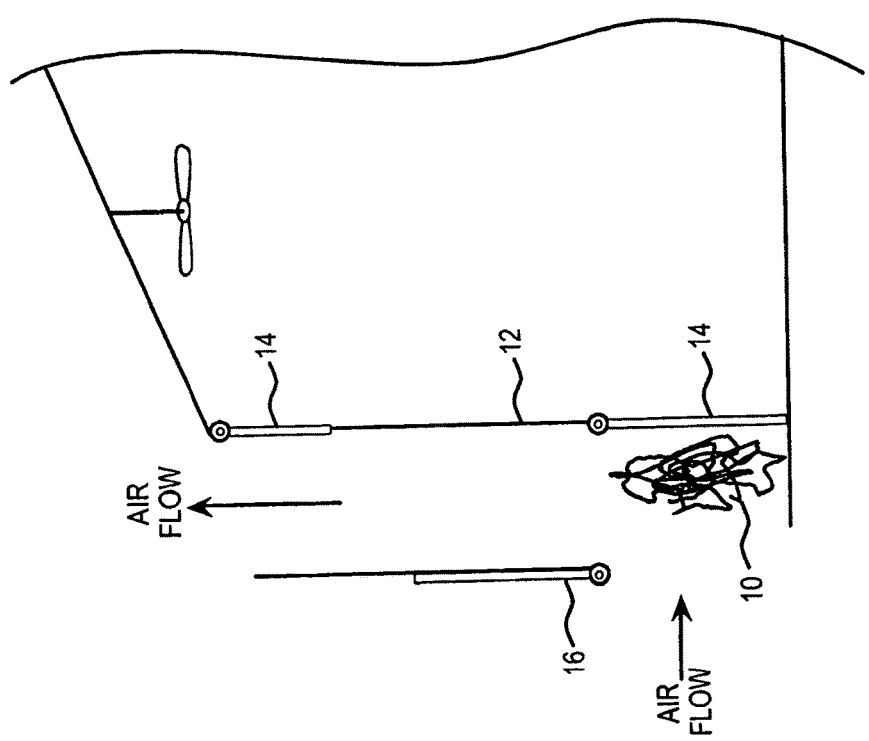
Figure 3B:
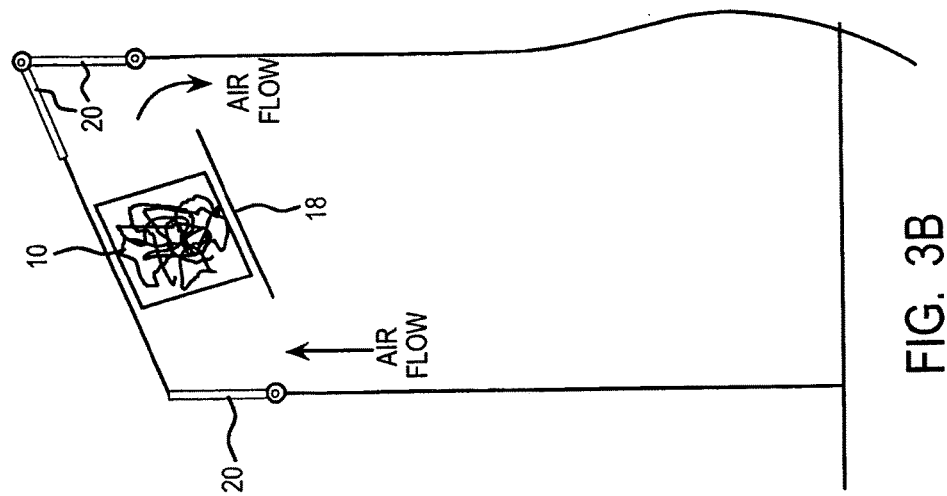
FIGS. 3*a* and 3*b* are schematic views of a $CO_2$ extractor/greenhouse feeder in accordance with the present invention, where filter units are located adjacent to the roof of the greenhouse.
Figure 3A:
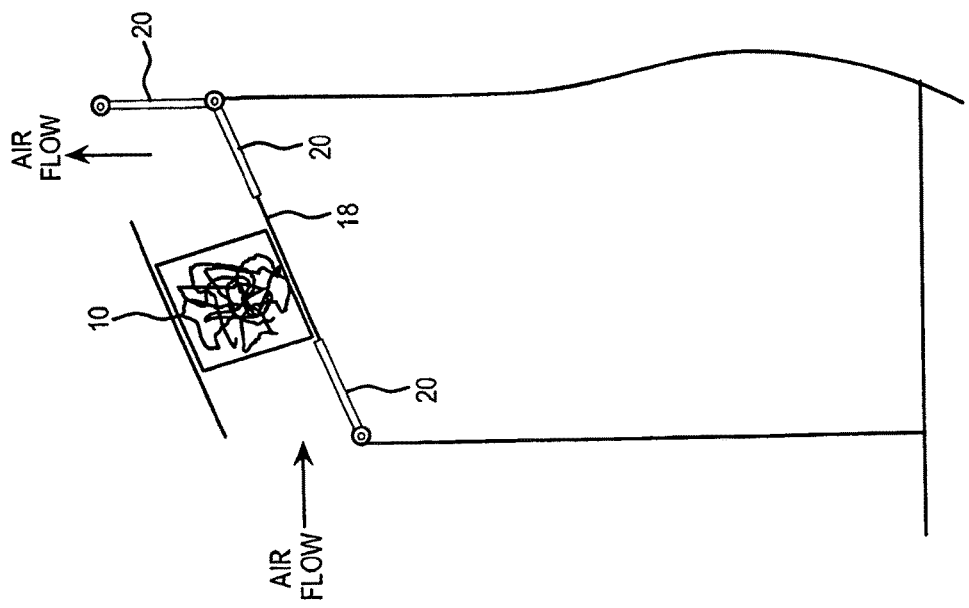

In one embodiment, as shown in FIGS. 2A and 2B, the filter units 10 are located adjacent an exterior wall 12 of a greenhouse, and outside air or greenhouse air routed selectively therethrough, as the case may be, via pivotally mounted wall panels 14. Alternatively, as shown in FIGS. 3A and 3B, the filter material 10 may be located exterior to and adjacent the roof 18 of the greenhouse, and outside air or greenhouse air routed selectively therethrough, as the case may be, via pivotally mounted roof panels 20.

Figure 4:
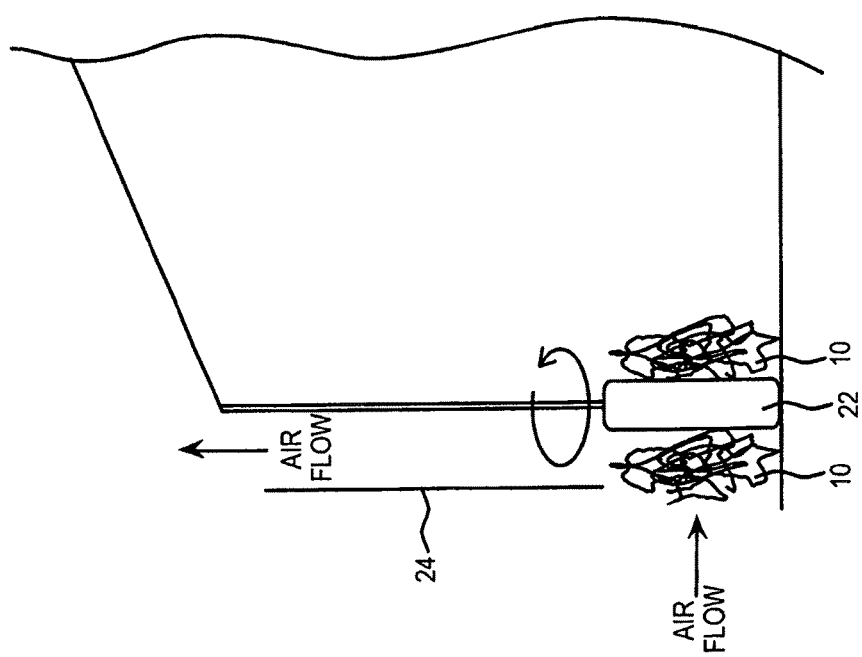
FIG. 4 is a schematic view of a $CO_2$ extractor/greenhouse feeder showing an arrangement of filter units according the present invention.

In yet another embodiment of the invention, shown in FIG. 4, the filter units 10, can be moved from outside the greenhouse where they extract $CO_2$ from the air to inside the greenhouse where they release the captured $CO_2$. One possible option for doing this is to have filter units mounted to pivotally mounted wall or roof panels 22 which can be reversed so that a filter unit on the outside of the greenhouse is exposed to the inside of the greenhouse and vice versa. Filter units that are inside the greenhouse can have air blown through them by a fan system. Filter units on the outside are exposed to ambient air. In a preferred embodiment, shown in FIG. 4, the filter units 10 on the outside are located adjacent the bottom end of a convection tower 24 that is solar driven. Preferably the inlets are installed at the bottom end of the convection towers where cool air enters and flows up the towers through natural convection.

Figure 5:
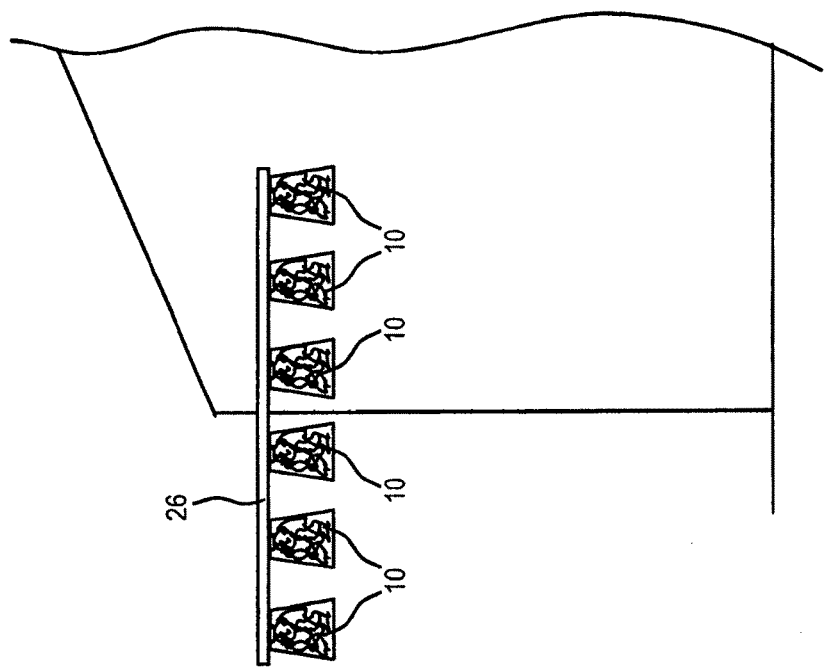
FIG. 5 is a schematic view of a $CO_2$ extractor/greenhouse feeder showing filter units arranged on a track according to an alternative embodiment of the present invention.

In yet another embodiment, shown in FIG. 5, the filter units 10 are moved in and out of the greenhouse, e.g. suspended from a track 26.

Figure 6:
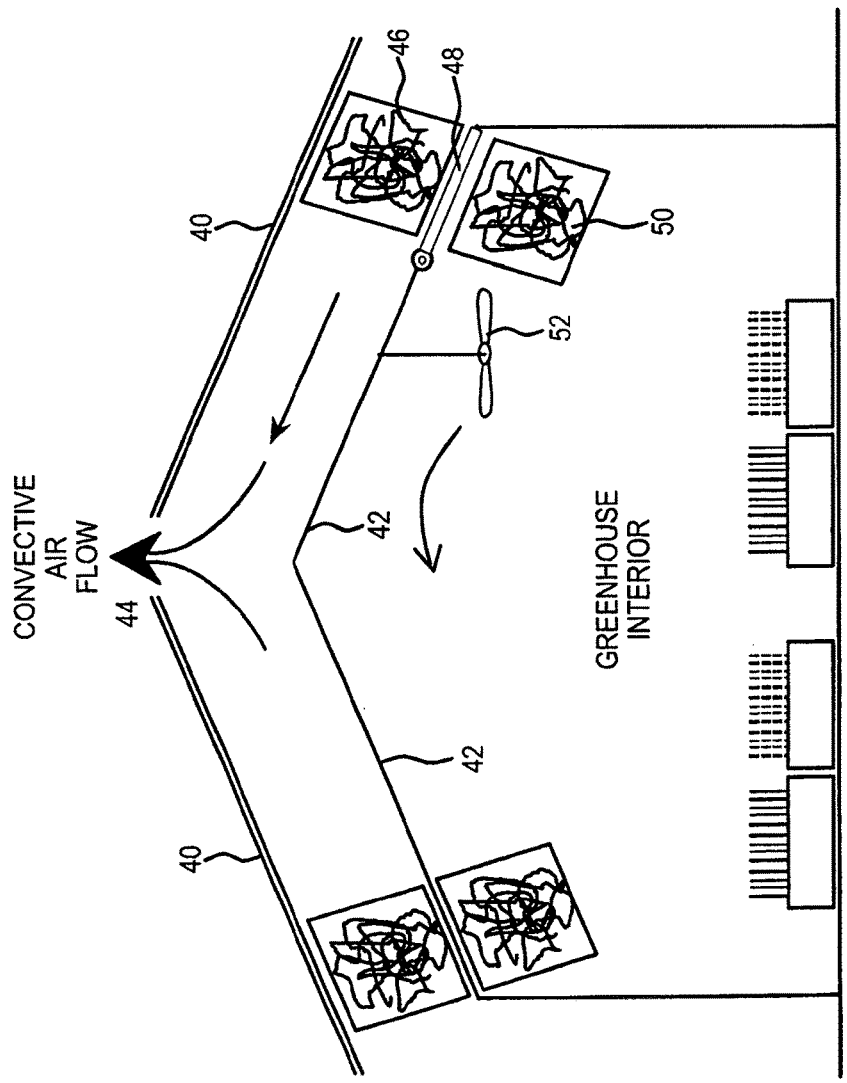
FIG. 6 is a schematic view of a $CO_2$ extractor/greenhouse feeder including convection towers according to an alternative embodiment of the present invention.

Referring to FIG. 6, yet another option for a greenhouse is to locate convection towers as double glass walls on the outside of the greenhouse, and use the convection stream generated to collect $CO_2$ on the outside. The double walls also serve to reduce the heatload on the interior during the day and thus reduce the need for air exchange which in turn makes it possible to maintain an elevated level of $CO_2$ in the greenhouse. The double glass walls also reduce heat loss during the night.

In this example a protective glass surface 40 may be provided to keep some of the heat away from the main roof of the glass house 42, causing a convective flow 44 of ambient air over the roof surface. The flow of ambient air is passed through a $CO_2$ absorbing filter medium 46, which can by some mechanism, such as a rotating roof panel 48, exchange places with a second like filter medium 50, where the air driven by fan 52 on the inside of the greenhouse is passed through the filter medium which gives up the $CO_2$ captured when the filter medium was exposed to ambient air outside the greenhouse. Because the air inside the greenhouse is moist, the $CO_2$ readily is released from the filter medium, and adds to the $CO_2$ available in the greenhouse.

An advantage of such a unit is that it could operate at elevated levels of $CO_2$ without combusting fuels. Because $CO_2$ is delivered to the inside of the greenhouse without blowing air into the greenhouse, this offers a possibility of reducing the exchange of air between the outside and the inside of the greenhouse, thus improving the heat management and moisture management of the greenhouse.

In a second exemplary embodiment of the invention, the $CO_2$ is extracted and delivered to an algal or bacterial bioreactor. This may be accomplished using conventional $CO_2$ extraction methods or by using an improved extraction method as disclosed in our aforesaid PCT applications or disclosed herein; e.g., by a humidity swing. A humidity swing is advantageous for extraction of $CO_2$ for delivery to algae because the physical separation allows the use of any collector medium without concern about compatibility between the medium and the algae culture solution. Transfer of gaseous $CO_2$ allows for the selection of any algae species, including macro and microalgae, marine or freshwater algae. Therefore, the selection of algae species to be grown could be solely dependent on environmental factors and water quality at the collector site. For example, the algae species to be used could be selected from algae naturally occurring at the site, which are uniquely adapted to the local atmospheric, environmental and water quality conditions.

There are two major advantages of transferring captured $CO_2$ in gaseous form. The first advantage is that the collector medium and/or the collector regeneration solution will not contact the algae culture solution and/or algae. The second is that all species of algae are capable of absorbing gaseous $CO_2$.

Depending on the $CO_2$ tolerance of particular algae cultures, the $CO_2$-enriched air can be pumped successively through several algae cultures in order of decreasing $CO_2$ tolerance and increasing $CO_2$ uptake efficiency. Alternatively the air can be diluted to the optimum $CO_2$ concentration.

Figure 7:
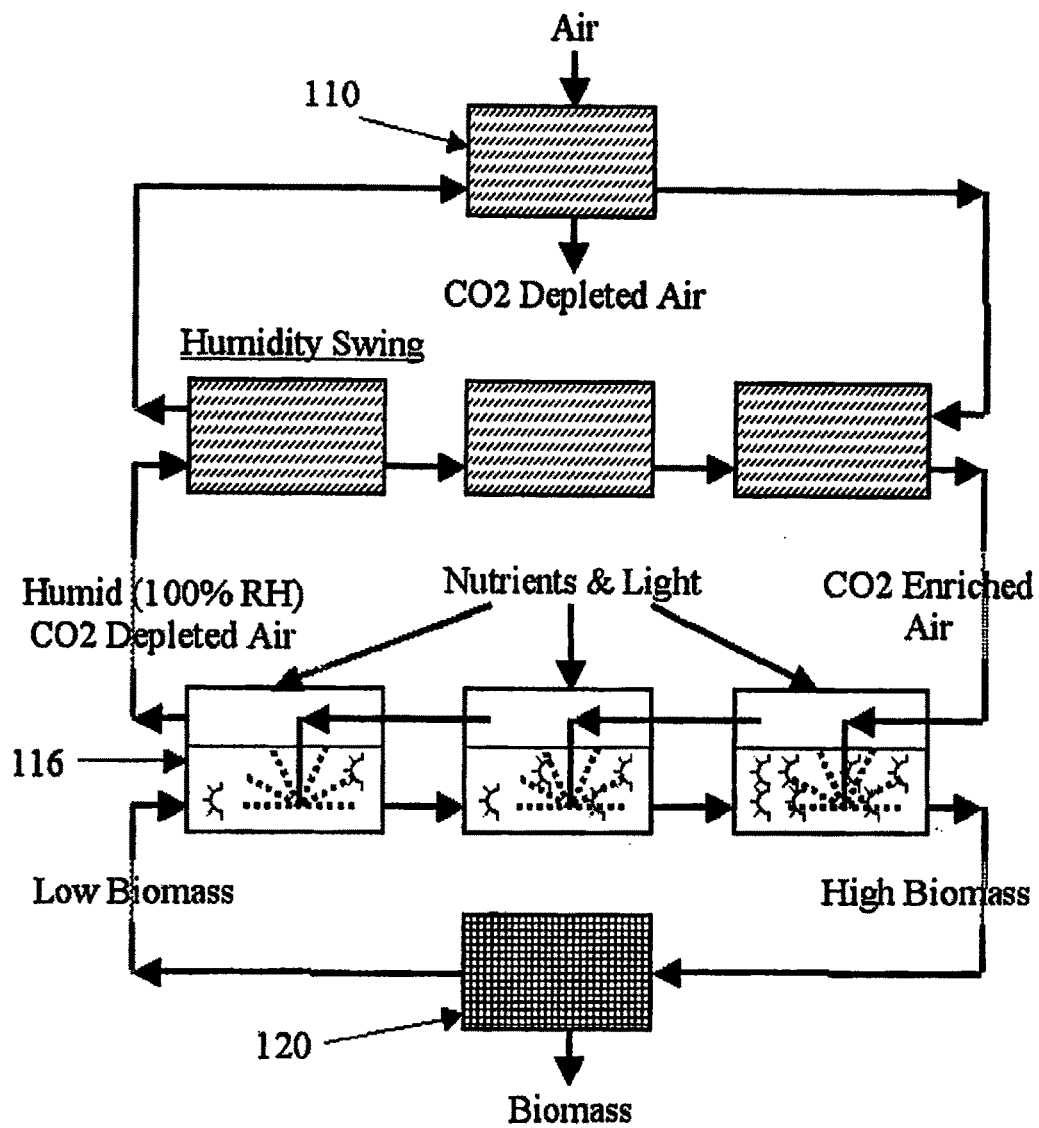
FIG. 7 is a schematic view of a $CO_2$ extractor and algae culture according to the present invention utilizing a humidity swing applied to a collector medium.

Referring to FIG. 7, one embodiment of the present invention takes advantage of the fact that gaseous $CO_2$ can be driven off the collector medium using a humidity swing. The humidity swing will transfer captured $CO_2$ as gaseous $CO_2$ from the collector 110 into the algae culture 116. An ion-exchange collector medium loaded with $CO_2$ will emit gaseous $CO_2$ when subjected to an increase in humidity or when wetted with water. And the collector medium will absorb more gaseous $CO_2$ when the humidity of the $CO_2$-supplying gas stream is decreased and/or the collector medium dries.

The present invention provides a common headspace above the collector medium and the algae culture. This exposes the algae to gaseous $CO_2$ while physically separating the collector medium from the algae culture solution. The headspace will be sealed from ambient air. The humidity is then raised in the closed headspace volume. Alternatively, the collector medium may be wetted. The $CO_2$ emitted from the collector medium quickly diffuses through the entire headspace and contacts the algae culture solution surface.

The $CO_2$ is then transferred into the algae culture either via gas diffusion or by bubbling the headspace gas through the algae culture solution using a recirculating pump. As the algae removes the $CO_2$ from the headspace, the collector medium continues to offgas until equilibrium is reached. The algae culture solution can be mechanically stirred. All other nutrients and light are provided to the algae as needed. The algae may then be collected in an algae harvester 120.

$CO_2$ concentrations in the headspace above wetted collector medium are up to 20%; or 0.2 atmosphere partial pressure. The concentration can be regulated by the volume to volume ratio of collector medium to headspace. Also the collector medium can release 60% of the captured $CO_2$ during a humidity swing/wetting.

Alternatively, it is also possible to pump gas from the collector medium volume through the algae culture in order to transfer the $CO_2$. If the algae pond is warm and moist the moisture from the algae pond may be sufficient to stimulate the release of $CO_2$ from the dry resin, again by the humidity swing mechanism.

Figure 8:
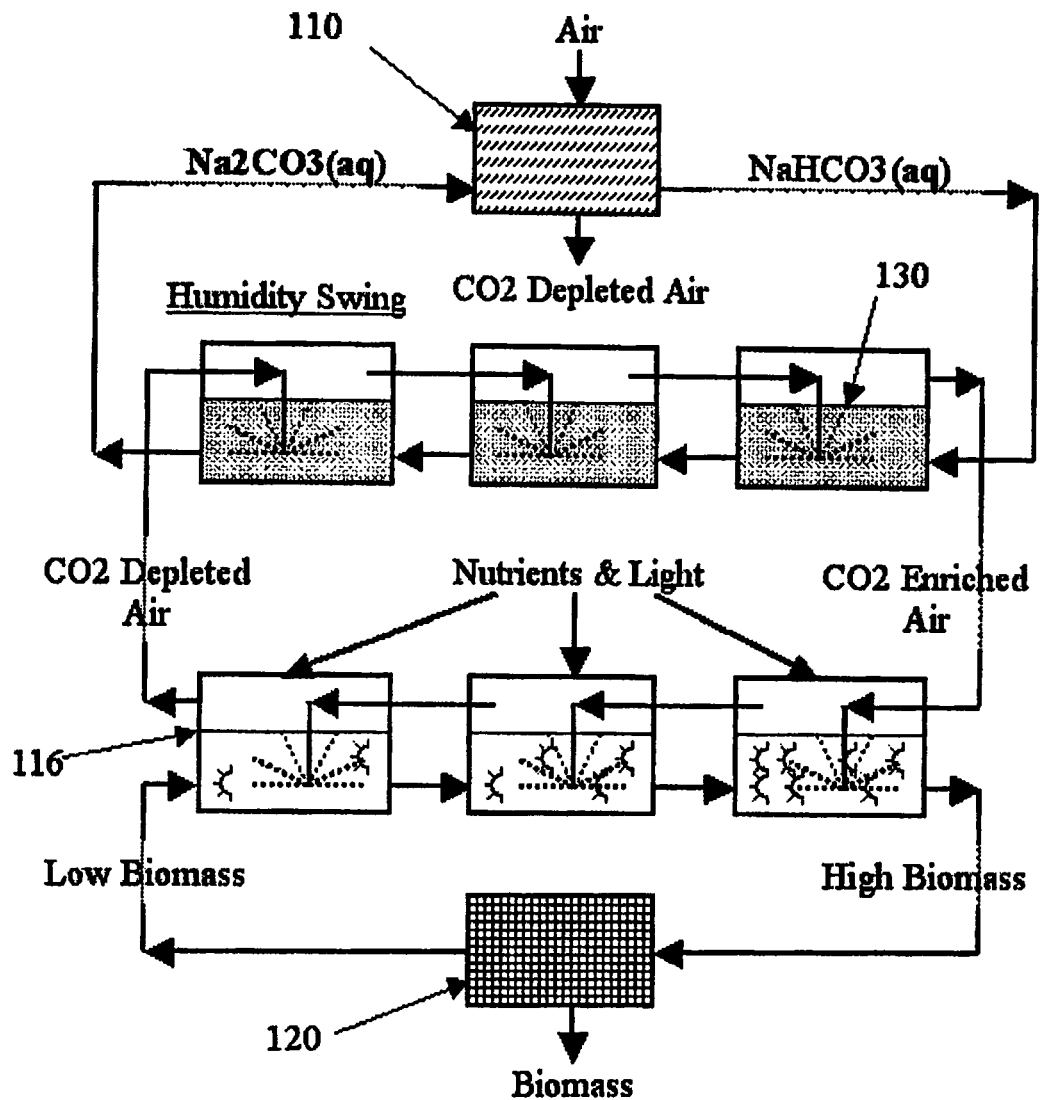
FIG. 8 is a schematic view of a $CO_2$ extractor and algae culture according to the present invention utilizing a humidity swing applied to a collector solution.

Referring to FIG. 8, in another embodiment of the present invention $CO_2$ concentrations in ambient air can saturate the ion-exchange medium with $CO_2$ to the level that the $CO_2$ is bound as bicarbonate anion. This embodiment provides regeneration of the collector medium using an alkaline solution. During the regeneration, the anion composition in the solution is changed to approximately 100% bicarbonate. Aqueous bicarbonate solution is not stable under atmospheric conditions and releases gaseous $CO_2$. Gaseous $CO_2$ emission can be enhanced by bubbling the headspace air through the solution using a recirculating pump.

An alternative embodiment provides a common headspace above the collector regeneration solution and the algae culture solution. This exposes the algae to gaseous $CO_2$, while separating the regeneration solution from the algae culture solution. In other aspects, this headspace operates similar to the headspace for the collector medium, as discussed above.

Figure 9:
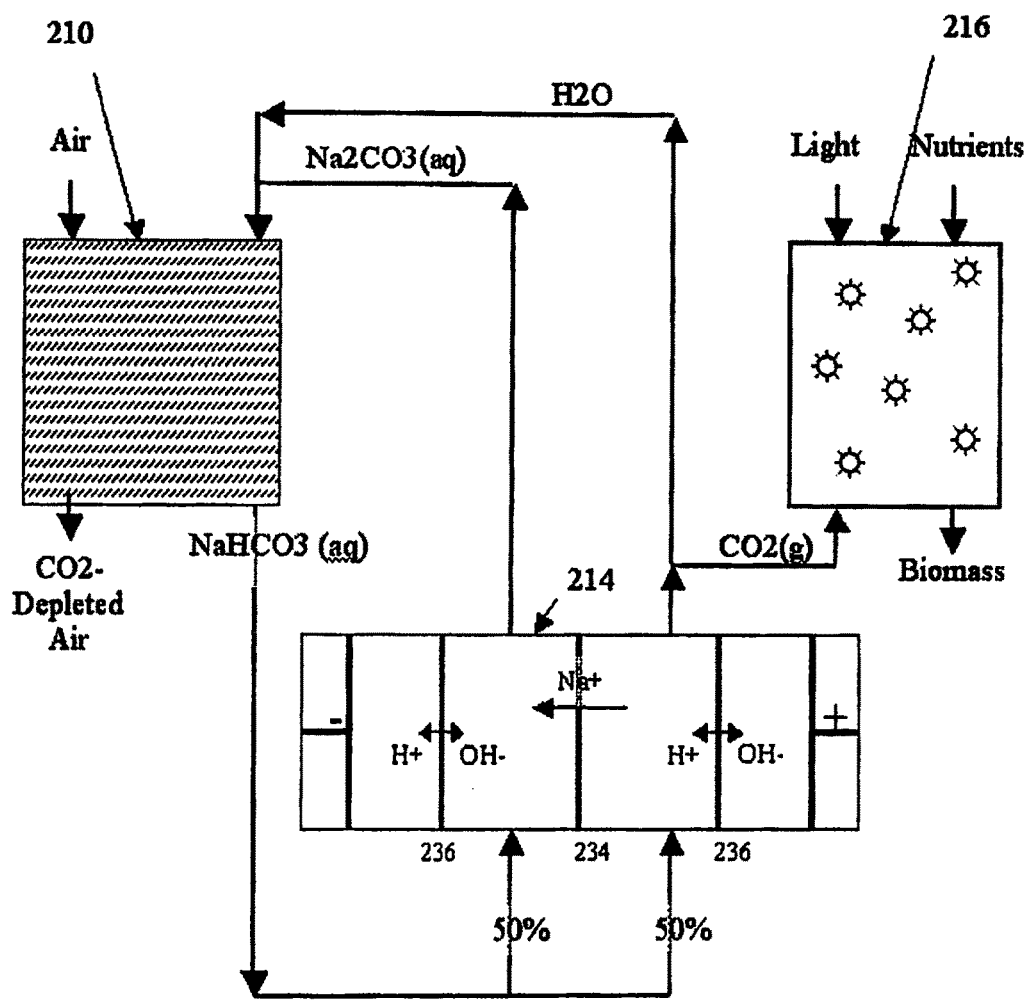
FIG. 9 is a schematic view of a $CO_2$ extractor and algae culture according to the present invention transferring gaseous $CO_2$ by an electro-dialysis process.

Referring to FIG. 9, another alternative embodiment of the present invention uses an electrodialysis (ED) process to free gaseous $CO_2$ from the loaded collector solution. The freed $CO_2$ is then transferred into an algae culture 216. The transfer of gaseous $CO_2$ from the collector 210 to the algae culture 216 through an electrodialysis (ED) process has the advantage that the collector solution or sorbent and algae culture solution are physically separated from each other at all stages of the process. This prevents the mixing of the two solutions and also prevents ion exchange between the solutions. The ED process has this in common with the humidity swing process. And as in the humidity process, the physical separation allows the use of any collector medium and any algae without regard to compatibility between the medium and the algae culture solution.

An alternative embodiment of the invention takes advantage of the fact that gaseous $CO_2$ can be driven off the collector regeneration solution using an ED process. In the ED process the loaded collector regeneration solution is split into two streams to enter the ED cell 214. Protons are added to the first stream across a secondary membrane 236 and the inorganic carbon is driven off as gaseous $CO_2$, while the sodium cations are transferred through a cationic membrane 234 into the second stream. In addition to the sodium ions, hydroxide ions are added to the second stream across another secondary membrane 236 thus neutralizing the bicarbonate in this stream to carbonate.

The first stream exits the ED cell as water or dilute sodium bicarbonate solution while the second stream exits as a concentrated sodium carbonate solution. The two streams are combined to form fresh collector solution. The gaseous $CO_2$ that is driven off the first stream is bubbled into the algae culture and is fixated as biomass.

As inorganic carbon is removed from the brine, the solution turns more alkaline and additional bicarbonate needs to be added to maintain the pH. Filtration allows us to recover some of the fluid and thus return water and sodium from the bioreactor. In one particular implementation the electrochemical cell will run between two separate fluid cycles, one fairly alkaline which runs between the collector and the base side of the electrochemical cell, and the other which runs at near neutral pH between the algae-reactor and the acidic side of the cell. Carbonic acid is transferred from the base side to the acid side of the cell. This step regenerates the wash and reloads the fluid with $CO_2$.

By feeding the bicarbonate sorbent to the algae, $CO_2$ can be removed from the sorbent without first converting the $CO_2$ back to $CO_2$ gas. Moreover, by selection of suitable sorbent material for the air capture side, the pH of the washing fluid can be kept relatively low, and if one uses algae that can tolerate a relatively high pH, the pH difference that needs to be made up by electrodialysis becomes relatively small, and in some implementations one can completely eliminate the dialysis cell.

Figure 10:
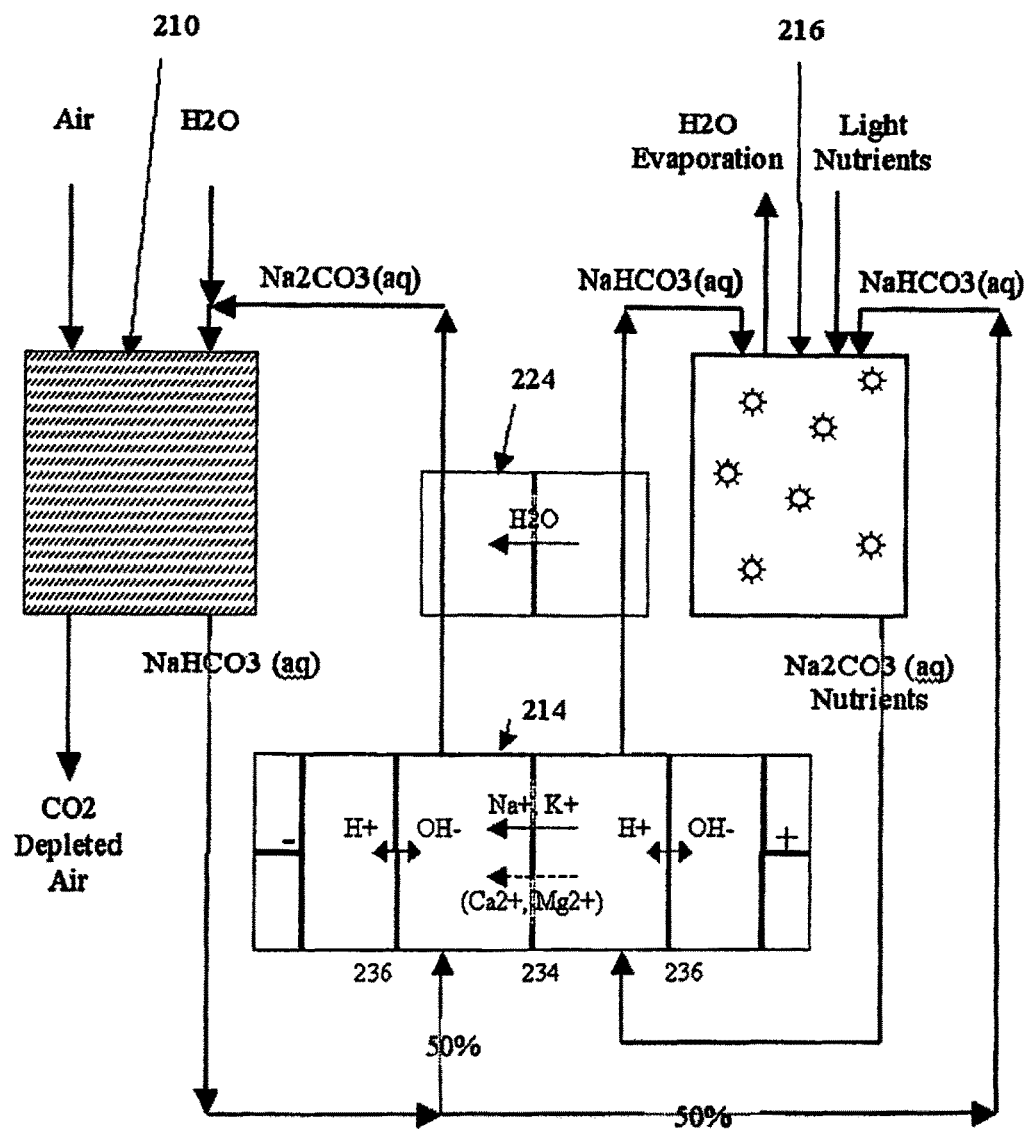
FIG. 10 is a schematic view of a $CO_2$ extractor and algae culture according to the present invention transferring bicarbonate by an electro-dialysis process.

Referring to FIG. 10, another embodiment of the present invention uses an ED process to decrease the bicarbonate concentration in the collector solution and to increase the bicarbonate concentration in the algae culture solution. The collector solution enters the ED cell 214 in the bicarbonate state, while the algae culture solution enters the ED cell in the carbonate state. When the fluids exit the ED cell, the collector solution is in the carbonate state and the algae culture solution is in the bicarbonate state.

Since cations are transferred from the algae culture solution to the collector solution, the algae culture solution is diluted to roughly half its normality, while the collector solution roughly doubles its normality. To make up for the sodium imbalance, half of the loaded collector solution (bicarbonate form) is transferred directly from the collector to the algae culture.

In a process scheme according to the present invention, cations are transferred from the algae solution into the collector solution through a cation exchange membrane 234. The algae culture solution contains predominantly sodium cations, but also potassium, magnesium and calcium ions as well as traces of other metal cations. The potential transfer of magnesium and calcium is of concern, since both ions form fairly insoluble carbonates and hydroxides. The formation of these salts, also known as scaling, can foul up the membranes in the ED cell and/or the collector medium.

Calcium and magnesium are added to the algae culture as mineral nutrients, at the start of an algae growing cycle. As the algae biomass increases calcium and magnesium are taken up into the biomass and their concentration in the algae culture solution decreases. Simultaneously, the culture solution pH increases as the bicarbonate solution is changed into a carbonate solution. If magnesium, calcium and carbonate ions are present above their solubility products, chemical precipitation will further decrease the magnesium and calcium ion concentrations.

The exhausted culture solution with decreased calcium and magnesium concentrations and a high pH is entered into the ED cell. There the culture solution is changed from a carbonate into a bicarbonate solution and its pH decreases accordingly. As the carbonate ion concentration decreases, the solution can hold more calcium and magnesium. So scaling is unlikely to happen in this part of the ED cell.

However, at the same time, cations including calcium and magnesium are transferred from the algae culture solution 216 to the collector solution half-cell of the ED. In this half-cell, the bicarbonate solution coming from the collector is changed into a carbonate solution: the carbonate concentration and the pH increase. Further, excess $H_2O$ may be removed from the bicarbonate solution using an osmosis cell 224.

The process is designed such that the pH of the exiting collector solution is close to the pH of the incoming algae solution. Therefore, scaling should not occur as long as everything is in balance. However, to keep perfect balance may not always be practical on the macro scale, and it may be impossible on the micro scale within the ED cell. It is possible that micro layers or pockets with increased hydroxide or cation concentrations are formed at the membrane surfaces. Increased concentrations at the surface of the membranes might cause scaling in the collector solution half-cell.

To minimize scaling, the flux of calcium and magnesium cations has to be minimized. This is a problem well known in the manufacture of salt from seawater, sodium hydroxide manufacture, and in processing of skim milk by electro dialysis (T. Sata, 1972; T. Sata et al., 1979, 2001; J. Balster, 2006). To minimize flux, the cationic membrane that separates the two half-cells has to be monovalent ion selective. In general, strong acid cation exchange membranes show larger transport numbers for divalent than monovalent ions. It is assumed that this is due to higher electrostatic attraction with the negatively charged fixed ion exchange sites. The prior art has shown that transport numbers for divalent cations decrease with lower charge density on membranes.

Two commercially available highly monovalent cation selective membranes have been identified as particularly suited for this process. One membrane is manufactured by Asahi Glass and is traded under the name Selemion CSV. The second is manufactured by Tokuyama Soda and is sold under the name Neosepta® CIMS. The transport numbers (t) for Selemion CSV are: t(Na)<0.92 and t(Ca, Mg)<0.04. The transport numbers for Neosepta CIMS are t(Na, K)=0.90 and t(Ca, Mg)=0.10. The transport numbers are defined as the equivalence flux of the cation divided by the total equivalence flux during electrodialysis.

This aspect of the invention uses a monovalent cation selective membrane to minimize the transfer of multivalent cations from the algae culture solution into the collector regeneration solution. Any scaling built up with time, will be removed using an acid solution.

Both the algae culture solution as well as the collector solution will be filtered before entering the ED cell to avoid membrane fouling with particles. Organic molecules will be scavenged from the algae culture solution by means of organic scavenging ion exchange resins.

Figure 11:
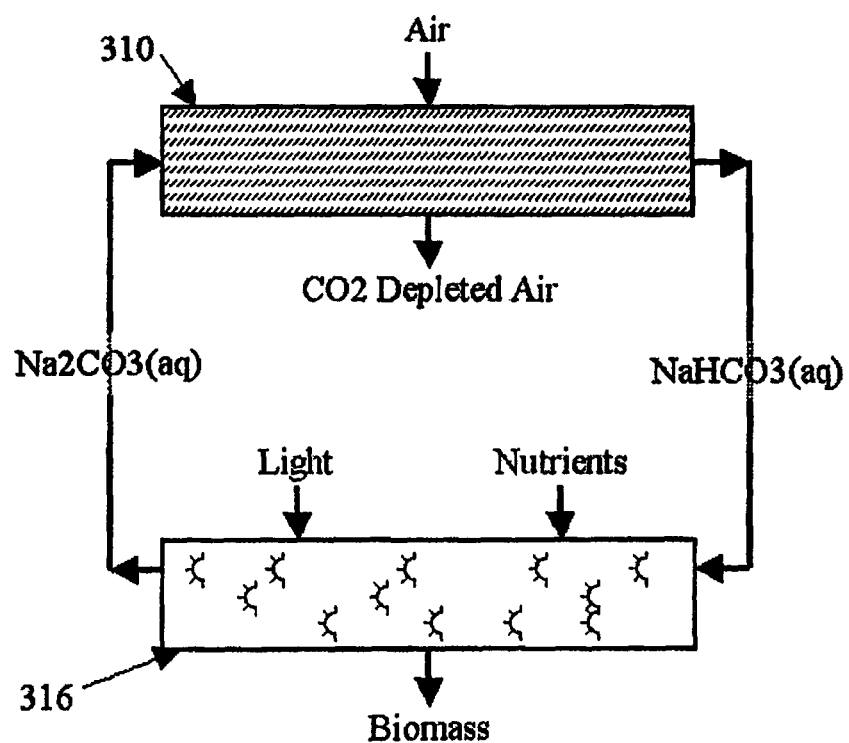
FIG. 11 is a schematic view of a $CO_2$ extractor and algae culture according to the present invention utilizing an algae culture for collector regeneration.

Referring to FIG. 11, in another embodiment of the present invention the $CO_2$ captured from air is transferred to the algae by feeding the loaded collector solution 310 to the algae. The loaded collector solution is enriched in sodium bicarbonate. Nutrients are added to the collector solution and it becomes the feed stock for algae. In this embodiment of the invention the solution feed is not recycled, so that the collector solution becomes a consumable.

In this process the algae culture solution 316 would increase in salt content as more and more sodium bicarbonate is added. The sodium bicarbonate is changed into carbonate during algae growth. To lower the carbonate concentration and to slow the salting, some of the remaining nutrients can be added as acids instead as sodium salts, which will convert carbonate ions to bicarbonate and minimize the addition of sodium.

Alternatively, the sodium bicarbonate sorbent is fed directly to an algae-reactor to supply the algae with $CO_2$, and the algae is removed for further processing, with the sodium bicarbonate being returned to the air extraction station.

Many algae can utilize bicarbonate as their carbon source. Also, some algae prefer bicarbonate over $CO_2$ as their carbon source. These are often algae that are indigenous to alkaline lakes, where inorganic carbon is predominantly present as bicarbonate. These algae can tolerate large swings in pH of 8.5 up to 11. Other algae can utilize $HCO_3^-$ as their carbon source, but require pH ranges below pH=9, which would require bubbling $CO_2$ through the bicarbonate/carbonate solution.

Algae use the carbon source to produce biomass through photosynthesis. Since photosynthesis requires $CO_2$ not bicarbonate, the algae catalyze the following reaction:

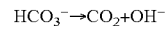

In the presence of $HCO_3^-$, this becomes:

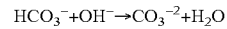

Algae growth in a bicarbonate solution induces the following changes in the solution: (1) a decrease in $HCO_3^-$ concentration; (2) an increase in $CO_3^{-2}$ concentration; and (3) an increase in pH.

Another embodiment the present invention uses an algae culture solution for collector regeneration. The collector medium in the carbonate form can absorb gaseous $CO_2$ from ambient air until the anion composition of the medium is nearly 100% bicarbonate. In this state the collector medium is fully loaded and $CO_2$ absorption comes to a halt. A carbonate solution can be used in regeneration to return the loaded collector medium to a carbonate form through ion exchange. The anion composition of the regeneration solution can be changed from 100% carbonate to nearly 100% bicarbonate through anion exchange with the fully loaded collector medium. In a counter-flow regeneration process the collector medium can be brought into a carbonate form, while the carbonate regeneration solution is changed into a bicarbonate solution. The regeneration solution is fully loaded when it is in the bicarbonate form, since it cannot remove any more bicarbonate from the collector medium.

The algae are introduced into the process to remove the captured $CO_2$ from the loaded regeneration solution by bicarbonate dehydration and neutralization (see above). The algae utilize the freed $CO_2$ for biomass growth. And the regeneration solution is changed from bicarbonate back into a carbonate solution.

In this process, the carbonate regeneration solution and the collector medium are recycled, while ambient air $CO_2$ is changed into algal biomass. This is shown in FIG. 11.

This process provides a cycle in which the ion exchange collector medium absorbs air $CO_2$. During the absorption the collector medium changes from carbonate to bicarbonate form. Then the regeneration solution pulls the air $CO_2$ from the loaded collector medium. In this exchange the collector medium is changed back into its carbonate form, while the regeneration solution changes from a carbonate to a bicarbonate solution. Finally, the algae remove the air $CO_2$ from the loaded regeneration solution by fixating it into biomass. In this step, the algae catalyze the reaction from bicarbonate to $CO_2$ and carbonate. The $CO_2$ carbon is bound into the algae biomass. The carbonate is left in solution. The resulting regeneration solution is then in carbonate form.

In another embodiment of the present invention, the algae culture solution is used as the collector regeneration solution. This means that the collector regeneration solution will in addition to carbonate contain other nutrients as required for the algae. Amongst these nutrients are anions that will compete with the carbonate anion during ion exchange with the collector medium.

In this process diatoms will not be used, since they require silica, which cannot be efficiently removed from the collector medium with a carbonate wash.

Other anionic nutrients typically found in algae culture mediums are: nitrate ($NO_3^-$), sulfate ($SO_4^{-2}$), and phosphate ($PO_4^{-3}$). Phosphorus may also be present as dibasic ($HPO_4^-$) or monobasic phosphate ($H_2PO_4^-$) depending on pH.

Nitrate, sulfate and phosphate concentrations for typical algae culture mediums are:

| Nutrient | Bold's Medium Molarity (M) | Zarouk's Medium Molarity (M) |
|---|---|---|
| NaHCO$_3$ | | 0.2 |
| NaNO$_3$ | 0.00882 | 0.029 |
| Mg SO$_4$—7H$_2$O | 0.0003 | 0.0008 |
| Fe SO$_4$—7H$_2$O | | 0.0018 |
| K$_2$SO$_4$ | | 0.0058 |
| Total S | Σ = 0.0003 | Σ = 0.0084 |
| K$_2$HPO$_4$ | 0.00043 | 0.0029 |
| KH$_2$PO$_4$ | 0.00129 | |
| Total P | Σ = 0.00172 | Σ = 0.0029 |

However, the prior art has shown that algae can grow at much lower nutrient concentrations than are contained in typical culture mediums.

To estimate the effect of the nutrient concentrations on the collector medium a nutrient-containing regeneration solution was mixed as follows: 0.14 M $CO_3^{-2}$, 0.04 M $NO_3^-$, 0.0017 M $SO_4^{-2}$ and 0.0017 M $H_2PO_4^-$. These represent the highest concentrations to be found in an algae culture medium and, therefore the worst-case scenario.

The collector medium was then flushed with this 'worst-case' solution until equilibrium was reached between the solution and the collector medium. At the pH of carbonate solution, phosphorus is present as dibasic phosphate ($HPO_4^{-2}$). Dibasic phosphate is basic enough to absorb $CO_2$. Therefore, the presence of dibasic phosphate anions on the collector medium will not lower the medium's $CO_2$ uptake capacity. It was determined that at equilibrium, about 50% of the collector medium's total exchange sites were occupied by carbonate and phosphate ions and 50% by nitrate and sulfate. Although the other nutrients outnumber carbonate, they do not completely replace it; instead, an anion equilibrium is reached that does not change with application of additional volumes of solution to the collector medium.

The experiments showed that in a worst-case scenario, the collector medium looses approximately 50% of its $CO_2$ uptake capacity. However, as determined by the research cited above, the nutrient concentrations in the solution can be depleted significantly during algae growth. For example, nitrate being by far the most abundant nutrient after inorganic carbon, can be reduced to 0.002 M, a mere 5% of the concentration used in the worst-case scenario experiment. And phosphate is reduced to 45% of the worst-case scenario.

Further, a collector medium washed with a nutrient-depleted solution will loose about 20% of its $CO_2$-uptake capacity. It is therefore possible to use the collector medium and wash it with a carbonate solution that has been derived from the algae growth medium.

The algae will secrete or release organic compounds into the solution during metabolism or decay. These organics will be scavenged from the solution, prior to applying the solution to the collector medium. Organics scavenging may be done with an adsorbent-type ion exchange resin or other processes.

Diatoms will not be used in this process, since they require silica, which cannot be efficiently removed from the collector medium using a carbonate wash.

A preferred algae for the present embodiment will have the following characteristics: they are adapted to high ionic strength liquids; they can grow in a pH range of 8.5 to roughly 11; they can tolerate a gradual pH change; they can use bicarbonate as their carbon source; they need little silica as a nutrient; they are capable of changing the pH of a solution from 8.5 to 11 or above; they can diminish nutrient concentrations to low levels; they can be used in biochemistry, agriculture, aquaculture, food, biofuels, etc.

Good candidates are, but are not limited to, algae that live in alkaline waters such as *Spirulina platensis, Spirulina fusiformis, Spirulina* sp., Tetraedron minimum and others.

There are many alternatives for this embodiment. Loaded collector solution (bicarbonate solution depleted in nutrients) is added to an algae culture together with fresh nutrients; the algal culture utilizes bicarbonate as its inorganic carbon source, by taking up about 50% of the bicarbonate carbon into its biomass and changing the remaining 50% to carbonate anions. Simultaneously, the algae culture depletes the nutrient concentrations in the solution. The culture is filtered, harvesting the algae biomass, while shunting the nutrient depleted solution towards the $CO_2$ collector. The nutrient depleted solution is cleaned of organics and other materials deleterious to the collector medium. The solution now enriched in carbonate is used to regenerate the collector. In the process each carbonate anion is replaced by two bicarbonate anions, until the collector solution is loaded. The loaded collector solution is added to the algae culture together with fresh nutrients as mentioned above.

The process can be run as a continuous loop or a batch process, whichever is more practical given location, algae type, etc. The process can employ algae culturing technologies already in use and proven or new technologies. For example, outdoor ponds have proven successful for the cultivation of *Spirulina, Chlorella vulgaris, Ankistrodesmus braunii* and other species in California, Hawaii, the Philippines and Mexico among other places. According to the National Renewable Energy Laboratory (NREL), outdoor ponds, e.g. so-called "race ponds", are the most efficient methods for growing a large biomass of algae.

The cultivation may use solar energy, artificial lighting or both dependent on the algae species and the place of operation. Algae culture solutions may be stirred to return algae to the zone of highest light ingress. Or the light might be brought into the algae cultures through mirrors, fiber optics and other means.

The algae can be either suspended in solution or immobilized. When suspended, algae follow their own growth patterns: single cells, colonies, clumped and so on. The natural growth pattern may not be the best match for the technology used. For example, small single celled algae may require elaborate harvesting processes.

Algae may naturally grow immobilized, if they attach themselves to surfaces, e.g., macro algae. Or algae can be immobilized: in beads using k-carragenan or sodium alginate, in polyurethane foam, on filter material, or as biofilms on column packing, or in other ways.

In an immobilized state, the algae may still be suspended, for example in bead form, and moving with the solution. Alternatively, the immobilized algae may be stationary in a column or other device, while the solution percolates past.

In another embodiment of the present invention, the collector medium is immersed into the Algae Culture. This can be done either in a batch process or in a continuous process. In a batch process, a batch of collector medium is alternatingly immersed in the algae culture and exposed to ambient air. In a continuous process, collector medium is continuously moved along a path on which it is alternatingly immersed in the algae culture or in exposed to air. The easiest implementation would be a disk of collector medium that rotates continuously around its center. The disk is submerged up to its center point in the algae culture, so that, at any time, one half of the collector medium is submerged in the liquid and the other half is exposed to air.

In this embodiment of the invention, collector medium could potentially be immersed in the algae culture solution at times of high nutrient content and at times of low nutrient content. The $CO_2$ capacity of the collector medium will, therefore, range from 50% to 80% of its full capacity. Air exposure times can be adjusted to account for the capacity decrease.

Figure 12:
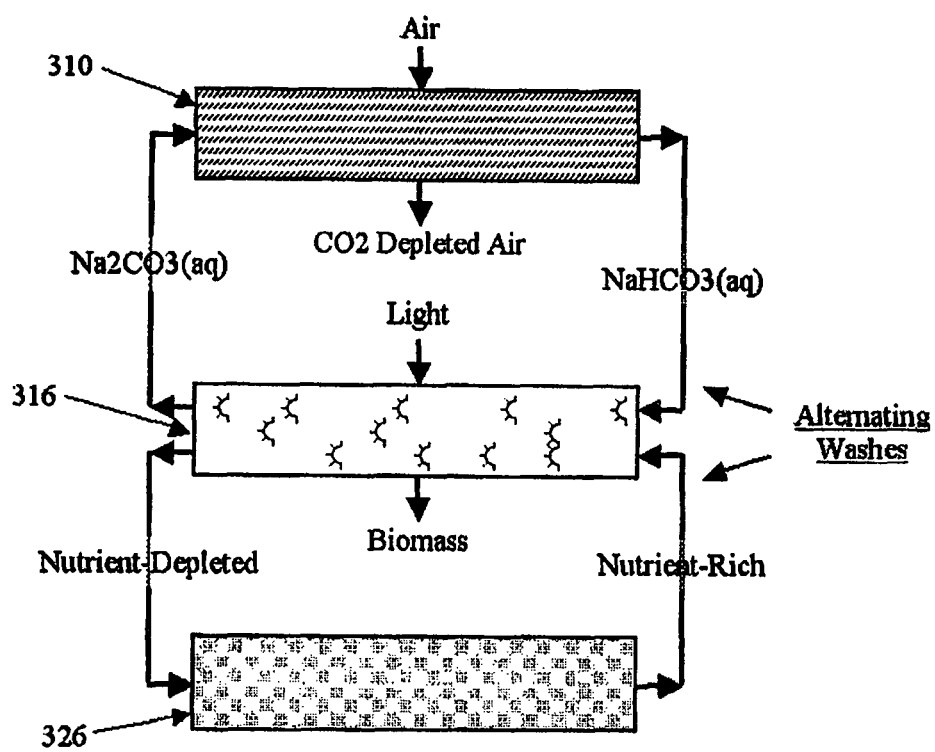
FIG. 12 is a schematic view of a $CO_2$ extractor and algae culture similar to FIG. 11 utilizing a nutrient solution.

Referring to FIG. 12, another embodiment of the present invention discloses sodium bicarbonate transferred from the collector solution to the algae by washing the algae in the loaded collector solution. However, nutrients will not be added to the collector solution. Instead, nutrients will be provided to the algae via a second separate wash cycle consisting of nutrient-rich carbon deficient solution.

In this process the algae will be immersed in nutrient-deficient bicarbonate solution (loaded collector solution) alternating with inorganic carbon-deficient nutrient solution 326. A short rinse cycle will be employed between washes. The rinse will be added to the solution of the preceding wash.

The cycles of nutrient and bicarbonate washes will be optimized for the algae species used. One or more algae species may be used either mixed or in series to optimize the conversion of the bicarbonate solution (loaded collector solution) to carbonate solution (fresh collector solution). The fresh collector solution may be filtered to remove particles and cleaned of organic molecules or other deleterious content prior to application on the collector medium.

The process can be designed to utilize suspended algae or immobilized algae. If the algae are suspended, the process has to be run as a batch process, and the algae have to be filtered from the solution. To ease filtering the algae may be "immobilized" in suspended beads, in order to increase the particle size.

A process involving immobilized algae can utilize algae that naturally grow immobilized, for example macro-algae that attach themselves to surfaces, or micro-algae that form biofilms etc.

In addition to others methods disclosed elsewhere in this application, the algae could be immobilized in columns, inclined raceways, ponds or other containers. The containers may be arranged to allow gravitational fluid flow Immobilization may be on the container walls and floors and/or on structures such as plates, packing etc. installed therein. Light is brought into the containers as needed either by natural lighting, artificial lighting, mirrors, fiber optics, etc.

Figure 13:
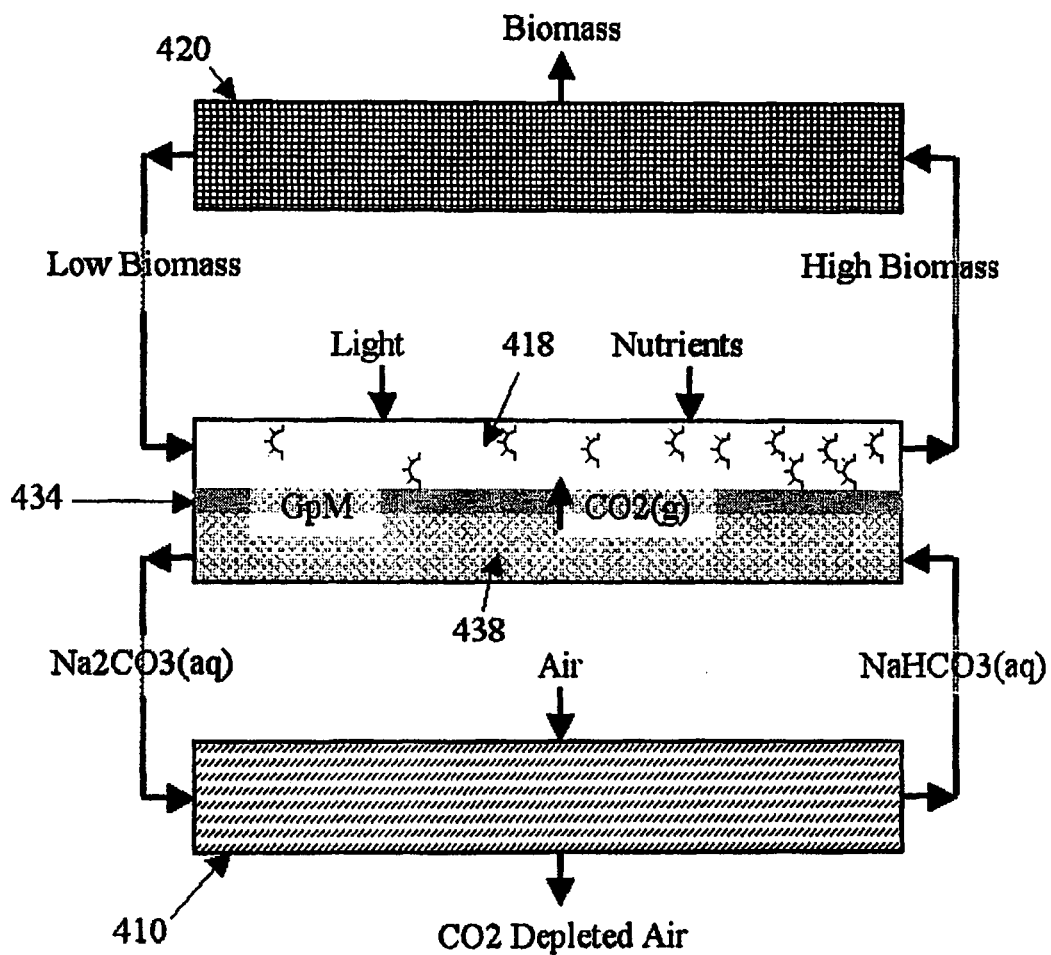
FIG. 13 is a schematic view of a $CO_2$ extractor and algae culture according to the present invention utilizing a gas-permeable membrane.

Referring to FIG. 13, another embodiment of the present invention transfers gaseous $CO_2$ from the loaded collector solution 410 to the algae culture solution 416 through a hydrophobic microporous membrane 434. Gaseous $CO_2$ can be transmitted from a bicarbonate solution through a hydrophobic membrane into a carbonate solution; and that the CO2 partial pressure differential between the two liquid streams is sufficient to drive the transfer. A transfer of water was noted from the more dilute solution to the more concentrated solution. As the membrane is hydrophobic, the transfer is of gaseous water molecules.

Simplified, the process can be described as two half-cells separated by a microporous, hydrophobic membrane. The first half cell 438 holds the loaded collector solution (sodium bicarbonate solution); while the second half cell 418 holds the algae culture (sodium carbonate solution including nutrients and algae).

The collector solution half-cell reaction is defined as follows:

$$2HCO_3^-(aq) \rightarrow CO_2(g) + CO_3^{-2}(aq) + H_2O$$

This is followed by $CO_2(g)$ diffusion through membrane into the algae culture half-cell. The reaction in the algae culture half-cell will follow in one of two ways:

Algae consume $CO_2(g)$ or $$CO_3^{-2}(aq) + CO_2(g) + H_2O \rightarrow 2HCO_3^-(aq)$$

and $$HCO_3^-(aq) + OH^- \rightarrow CO_3^{-2}(aq) + H_2O$$

As can be seen from the half-cell reactions, the pH in the collector solution will continuously increase as bicarbonate is reacted into carbonate through off-gassing of gaseous $CO_2$. In a balanced system the algae culture solution will not change its pH as the gaseous $CO_2$ is fixated by algae growth into biomass. The algae culture will preferably be close to a carbonate solution. In that case, it would not contain appreciable amounts of bicarbonate. This condition would maximize the gaseous $CO_2$ partial pressure differential between the collector solution and the algae culture.

The physical arrangement of the two half-cells can take many forms including but not limited to the few arrangements described herein. Each arrangement will optimize the ratio of liquid-membrane contact area to solution volume. In general it is advantageous to run the collector solution through membrane channels submerged in the algae culture, since this will enable light supply to the algae culture. In cases where the algae culture is contained in membrane conduits, light will be supplied inside the conduits.

The membrane conduits can take many shapes. For example, they can be parallel membrane sheets, causing a sheet flow of solution sandwiched between the membranes. Or they could be tubular with the tube cross-section taking varying forms, for example round, square, rectangular, corrugated, etc. Tubes could form a spiral or other shapes to increase their path length through the solution.

The process can be run as a batch procedure, a continuous loop process or any combination thereof. Light and nutrients will be supplied as needed.

In a pure batch process, a batch of loaded collector solution is brought in membrane contact with a batch of algae culture and left to reach equilibrium.

In a pure continuous loop process both solutions flow in continuous loops. The loaded collector solution would flow along a membrane path, throughout which it transfers its gaseous $CO_2$ to the algae solution; from there it enters the regeneration system for the collector medium, where it loads up with $CO_2$ to then reenter the membrane conduit. The algae solution will flow past the membrane path with algae fixating the gaseous $CO_2$; from there it will enter a harvesting system 420, where some or all algae are removed from the solution to then reenter the membrane system for renewed $CO_2$ fixation and algae growth. Continuous flow or loop processes may use concurrent flow or counter-current flow of the two streams.

The major advantage of transferring the $CO_2$ through a hydrophobic membrane is that ions cannot cross from the algae culture into the collector solution. The cations contained in the algae solution include earth alkali metals that can cause scaling along the collector solution path as the pH increases. The anions, such as nitrate and sulfate, contained in the algae solution compete with carbonate on the collector medium thus lowering the $CO_2$ holding capacity of the collector medium. Therefore, it is advantageous to keep the ions from entering the collector solution. Since ions, which constitute the nutrients for the algae, cannot cross into the collector solution, the nutrient content of the algae culture can be permanently kept at the optimum concentration for algae growth.

In addition, the prior art discloses hydrophobic membranes that are also organophobic and can impede the transfer of organic molecules from the algae solution to the collector solution. Any organics that may be transferred into the collector solution will be removed from the collector solution before it enters the collector medium. For example, this can be done by scavenging the organic compounds onto ion exchange resins.

The membrane will be selected for its hydrophobicity, $CO_2$ permeability, organophobicity, and water breakthrough pressure. The preferred algae for this process are those that thrive in carbonate solutions and can both utilize gaseous $CO_2$ and bicarbonate. However, other algae can also be used to optimize the complete process.

Figure 14:
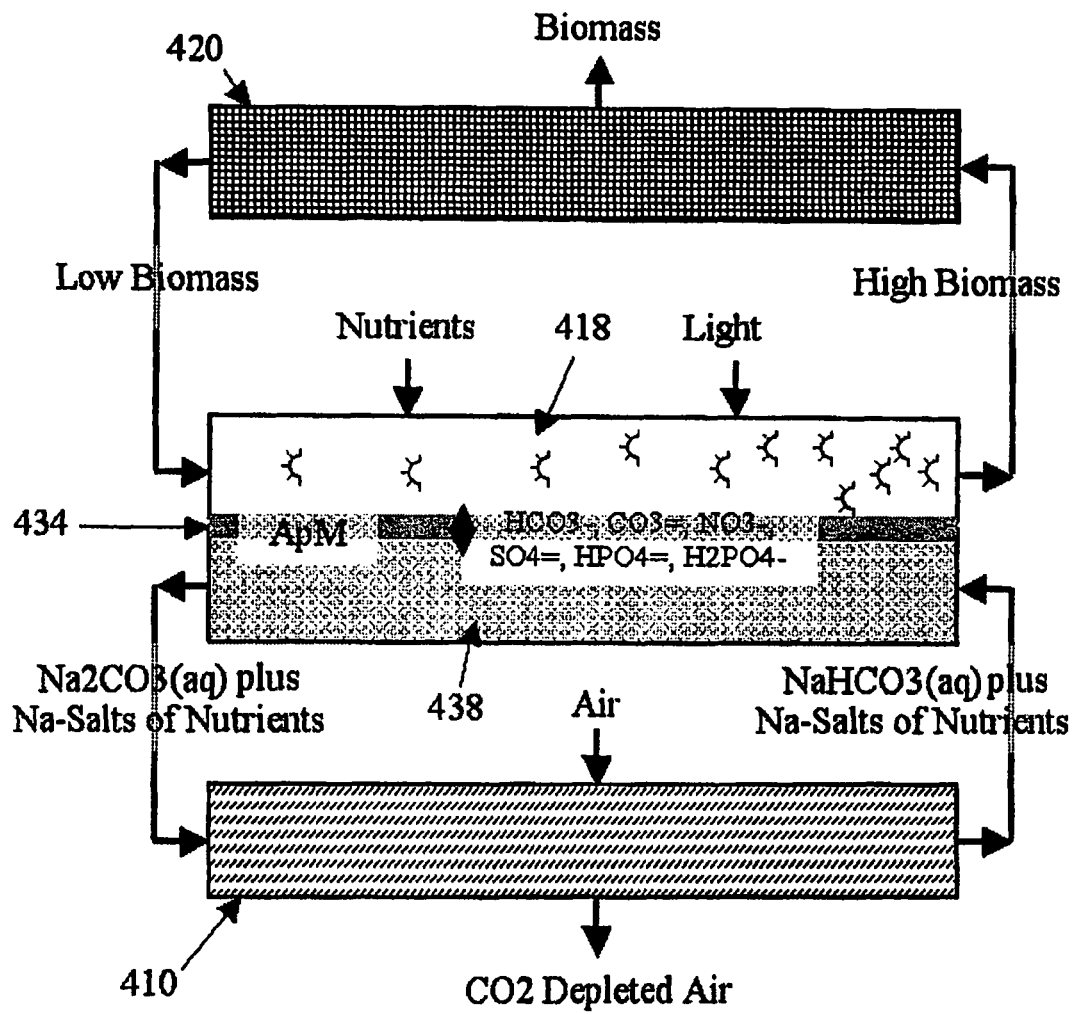
FIG. 14 is a schematic view of a $CO_2$ extractor and algae culture according to the present invention utilizing an anion-permeable membrane.

Referring to FIG. 14, another embodiment of the present invention transfers bicarbonate from the collector solution 410 into the algae culture solution 418 through an anion permeable membrane. The collector solution is brought into contact with one side of the anion permeable membrane 434, while the algae culture solution is brought into contact with the other side of the membrane.

The solutions exchange anions along concentration gradients. To optimize this ion exchange, the solutions can be run past the membrane in a counter-current. The solutions can also be run co-current to optimize other parts of the system. Alternatively, the process can be set up as a batch process rather than a continuous flow process.

Figure 15:
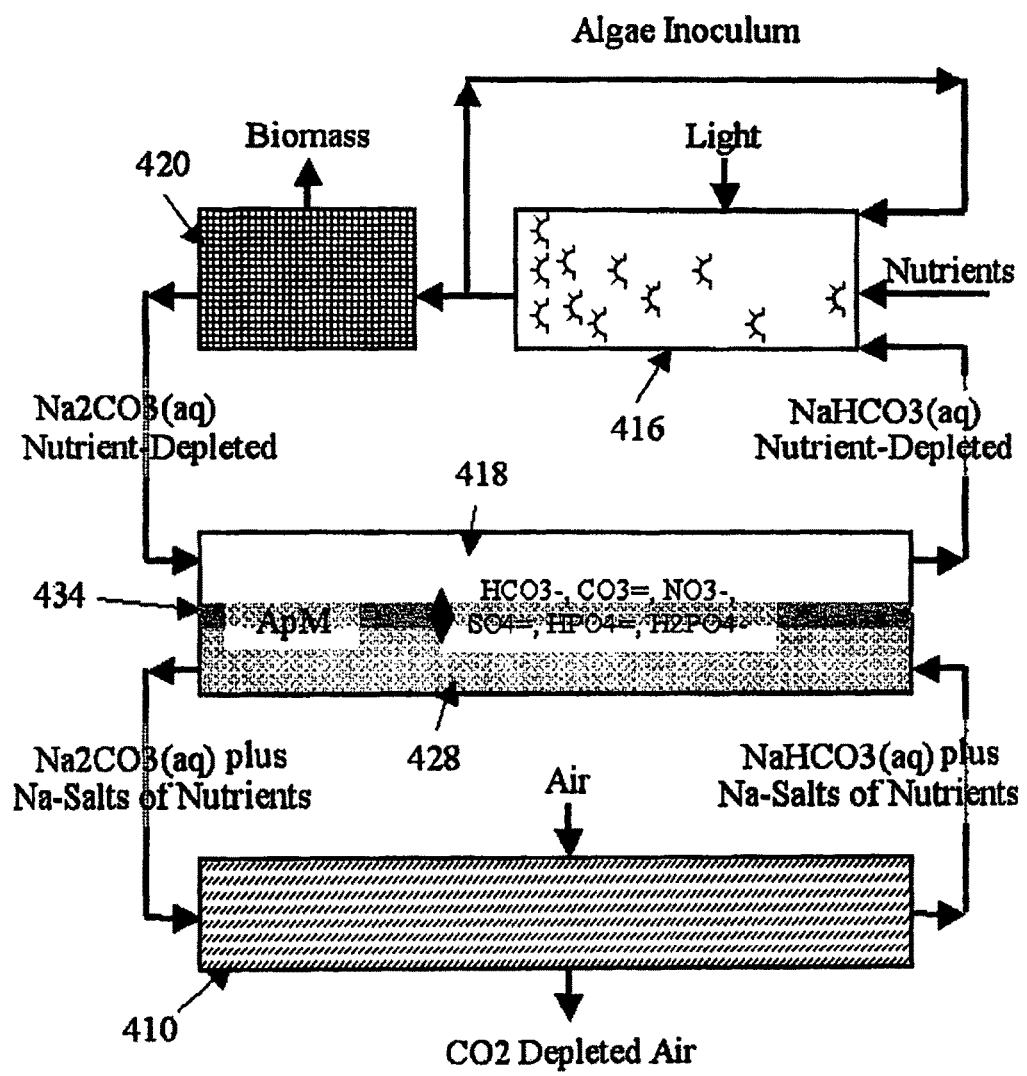
FIG. 15 is a schematic view of a $CO_2$ extractor and algae culture similar to FIG. 14.

The algae culture solution can be entered into the anion exchange process with algae suspended in the solution or without the algae. See FIG. 15. Dissolved organic compounds can be removed from the algae culture solution prior to entering the membrane chamber.

Nutrient effects apply as discussed above. If the whole algae culture including algae is entered into the membrane exchanger, the nutrient concentration will be high and the collector solution will gain high nutrient concentrations. This may lead to a reduction in the collector medium's $CO_2$ uptake capacity of up to 50%. If the culture solution without algae is entered into the membrane exchanger, the process can be set up such that nutrient-depleted solution is entered, in which case the collector capacity might be reduced by up to 20%.

Cations will not be exchanged between the two solutions, which greatly reduces the potential for scaling.

Alternatively, one can inject captured $CO_2$ directly into an algae-bio-reactor synthetic fuel production unit. A particularly simple design is to provide a paddle wheel or disks or the like carrying humidity sensitive ion exchange resins that are exposed primarily above the water surface where $CO_2$ is extracted from the air, and are slowly rotated to dip a portion under the water surface where the $CO_2$ is released to provide high air-to-water transfer rates for the $CO_2$.

Figure 16:
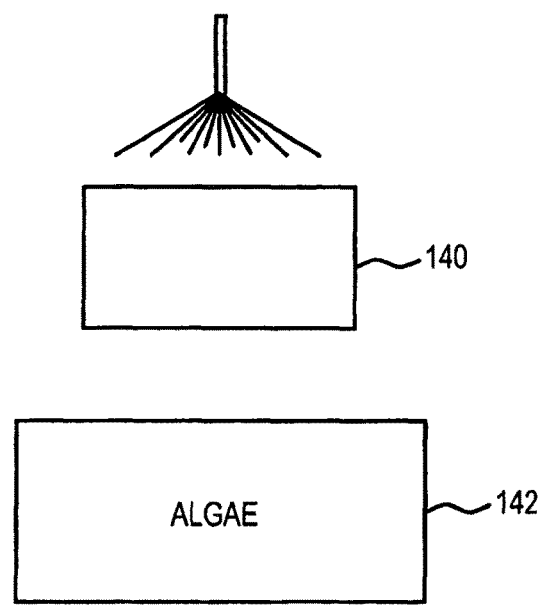
FIG. 16 is a schematic view of a $CO_2$ extractor and algae culture according to the present invention including a shower.

Referring to FIG. 16, in another embodiment it is possible to shower an ion exchange resin with slightly alkaline wash water at an extraction station 140, similar to the first exemplary embodiment, to make up evaporative or production losses of water from the bioreactor. As the wash water trickles over the primary resin, it will pick up bound $CO_2$ and dribble it into the bioreactor system 142.

Figure 17:
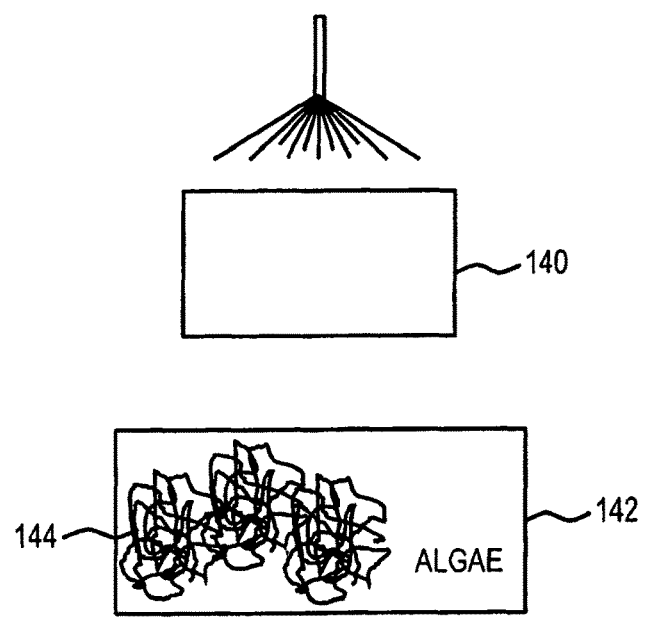
FIG. 17 is a schematic view of a $CO_2$ extractor and algae culture similar to FIG. 16.

Alternatively, as shown in FIG. 17, resins 142 may be added to the water at night to retain the $CO_2$ that may be lost from the algae due to respiration. Thus we can improve the $CO_2$ uptake efficiency of the algae, by preventing the release of nighttime $CO_2$ from the bioreactor. In such embodiment, a secondary resin acts as a carbon buffer in the system. At night this buffer stores the $CO_2$ released by the algae, while during the day it provides $CO_2$ to the algae, while its $CO_2$ content may be supplemented by the $CO_2$ that is collected by the air collector. Once captured, the $CO_2$ is transferred to the resin from a more concentrated wash used in regenerating the primary resin. Water filtration to keep algae out of the air collector generally is not a problem due to the fact that the air-side primary resin is designed to completely dry out in between cycles.

This transfer to the secondary resin also could be accomplished without direct contact in a low-pressure closed moist system, such as shown in FIG. 1, by performing a humidity swing that avoids direct contact with the water. While such a system loses the aforementioned advantage of not bringing $CO_2$ back to the gas phase, it will have other advantages in buffering the algae pond at a constant pH, without the use of chemicals.

In a preferred embodiment of the invention, as seen in FIG. 18, in order to reduce water losses, increase yield, and better confine the algae, we employ bioreactors 150 with light concentrators 152. Such systems may be built from glass tubes surrounded by mirrors, or mirror or reflector systems that feed into fiber optic light pipes that distribute the light throughout a large liquid volume. The advantage of the use of a bioreactor with light concentrators is that they greatly reduce the water surface and thus reduce water losses. Thus, the $CO_2$, can be collected nearby without directly interfering with the algae reactors. Indeed air collectors could take advantage of mirror systems for guiding air flows.

Algae typically fixate $CO_2$ during times of light influx, and respire $CO_2$ during dark cycles. The $CO_2$ is captured by adding additional collector medium to the system in strategic places. The collector medium can, for example, be immersed in the algae culture. In this case, it will store bicarbonate and release carbonate during respiration as the culture solution pH decreases, and it will release bicarbonate and store carbonate during photosynthesis as the culture solution increases in pH.

Collector medium can also be placed in the air space in proximity of the algae culture to absorb $CO_2$ that has been released from the culture solution. This will be especially efficient in closed structures. Collector medium placed in the proximity of the culture solution will be regenerated using one of the processes described above.

This application is intended to include any combination of the inorganic carbon transfer methods described in this patent using any combination of algae cultures as required to optimize the process. Optimization includes but is not limited to optimization of the carbon transfer efficiency, carbon transfer rate, market value of the biomass (for example oil content, starch content etc.), algae productivity efficiency, and algae growth rate under any climate conditions or climate-controlled conditions.

While the invention has been described in connection with a preferred embodiment employing a humidity sensitive ion exchange resin material for extracting $CO_2$ from ambient air and delivering the extracted $CO_2$ to a greenhouse by humidity swing, advantages with the present invention may be realized by extracting carbon dioxide from ambient air using a sorbent in accordance with the several schemes described in our aforesaid PCT Application Nos. PCT/US05/29979 and PCT/US06/029238, and releasing the extracted $CO_2$ into a greenhouse by suitably manipulating the sorbent.

The invention claimed is:

1. An apparatus for the capture of carbon dioxide from ambient air outside of a greenhouse and transferring said carbon dioxide to air within the interior of said greenhouse comprising:
   a solid, humidity sensitive ion exchange resin adapted for alternating fluid communication with air within the interior of the greenhouse and fluid communication with ambient air outside of the greenhouse; and
   a moisture source that exposes the ion exchange resin to humidity or water when the ion exchange resin is in fluid communication with the interior of the greenhouse.

2. The apparatus of claim 1, wherein the ion exchange resin comprises a heterogenous ion exchange membrane.

3. The apparatus of claim 1, wherein the ion exchange resin comprises a strong base resin.

4. The apparatus of claim 1, wherein the ion exchange resin is moveable from the outside to the inside of the greenhouse.

5. The apparatus of claim 4, wherein the ion exchange resin is mounted on a moveable fixture built into a wall of the greenhouse.

6. The apparatus of claim 1, wherein the ion exchange resin is included in an extractor that is located adjacent a lower end of a convection tower built adjacent the greenhouse.

7. The apparatus of claim 1 wherein the ion exchange resin comprises a first store of ion exchange resin; and the apparatus further comprises a second store of ion exchange resin, and a selectively closed loop recirculation system for selectively recirculating air through the first store and the second store.

8. The apparatus of claim 7, including flow valves for controlling recirculation.

9. The apparatus of claim 7, wherein the first store of ion exchange resin and the second store of ion exchange resin each comprise a strong base Type 1 or Type 2 functionality ion exchange resin.

10. The apparatus of claim 3, wherein the ion exchange resin comprises a strong base Type 1 or Type 2 functionality ion exchange resin.

11. The apparatus of claim 1, wherein said ion exchange resin comprises Anion 1-200 ion exchange membrane material.

12. The apparatus of claim 1, further comprising a sorbent to which released carbon dioxide may be transferred.

13. The apparatus of claim 12, wherein said sorbent is selected from the group consisting of: a liquid amine, an ionic liquid, a solid $CO_2$ sorbent, lithium zirconate, lithium silicate, magnesium hydroxide, and calcium hydroxide.

14. The apparatus of claim 12, wherein said sorbent comprises a second ion exchange resin.

15. The apparatus of claim 1, wherein said ion exchange resin comprises a material from which 60% of carbon dioxide that is captured thereby is releasable by wetting or exposure to humidity.

16. The apparatus of claim 1, further comprising a device for driving the ambient air outside of the greenhouse into fluid communication with the ion exchange resin, wherein said device is selected from a thermal convection device or one or more fans.

17. The apparatus of claim 1, further comprising a fan for driving the air within the interior of the greenhouse into fluid communication with the ion exchange resin.

18. The apparatus of claim 17, wherein the fan is integrated as part of a climate control system for the greenhouse.

19. The apparatus of claim 1, wherein the ion exchange resin comprises a resin and an inactive polymer carrier.

20. The apparatus of claim 19, wherein the inactive polymer carrier is a polypropylene binder.

* * * * *